United States Patent
Dairoku et al.

(10) Patent No.: US 7,153,910 B2
(45) Date of Patent: *Dec. 26, 2006

(54) WATER-ABSORBENT RESIN GRANULE-CONTAINING COMPOSITION AND PRODUCTION PROCESS FOR WATER-ABSORBENT RESIN GRANULE

(75) Inventors: Yorimichi Dairoku, Himeji (JP); Kunihiko Ishizaki, Suita (JP); Takumi Hatsuda, Takasago (JP); Kazuhisa Hitomi, Himeji (JP); Katsuhiro Kajikawa, Himeji (JP); Soichi Yamada, Himeji (JP)

(73) Assignee: Nippon Shokubai: Co., Ltd., Osaka (JP)

( * ) Notice: Subject to any disclaimer, the term of this patent is extended or adjusted under 35 U.S.C. 154(b) by 488 days.

This patent is subject to a terminal disclaimer.

(21) Appl. No.: 10/212,438

(22) Filed: Aug. 5, 2002

(65) Prior Publication Data

US 2003/0008946 A1   Jan. 9, 2003

Related U.S. Application Data

(60) Division of application No. 09/649,418, filed on Aug. 26, 2000, now Pat. No. 6,458,921, which is a continuation of application No. 09/093,476, filed on Jun. 9, 1998, now Pat. No. 6,228,930.

(30) Foreign Application Priority Data

| Jun. 18, 1997 | (JP) | ................................ 09-160964 |
| Jun. 23, 1997 | (JP) | ................................ 09-165666 |
| Jan. 9, 1998 | (JP) | ................................ 10-003327 |

(51) Int. Cl.
*C08F 20/02* (2006.01)

(52) U.S. Cl. .................. 525/329.7; 528/481

(58) Field of Classification Search .............. 525/329.7
See application file for complete search history.

(56) References Cited

U.S. PATENT DOCUMENTS

| 4,043,952 A | 8/1977 | Ganslaw et al. |
| 4,051,086 A | 9/1977 | Reid |
| 4,123,397 A | 10/1978 | Jones |
| 4,666,983 A | 5/1987 | Tsubakimoto et al. |
| 4,734,478 A | 3/1988 | Tsubakimoto et al. |
| 4,755,560 A | 7/1988 | Ito et al. |
| 4,771,105 A | 9/1988 | Shirai et al. |
| 4,950,692 A | 8/1990 | Lewis et al. |
| 5,002,986 A | 3/1991 | Fujiura et al. |
| 5,140,076 A | 8/1992 | Hatsuda et al. |
| 5,244,735 A | 9/1993 | Kimura et al. |
| 5,248,709 A | 9/1993 | Brehm |
| 5,324,561 A | 6/1994 | Rezai et al. |
| 5,342,899 A | 8/1994 | Graham et al. |
| 5,369,148 A | 11/1994 | Takahashi et al. |
| 5,384,368 A | 1/1995 | Date et al. |
| 5,385,983 A | 1/1995 | Graham |
| 5,409,771 A | 4/1995 | Dahmen et al. |
| 5,422,405 A | 6/1995 | Dairoku et al. |
| 5,486,569 A | 1/1996 | Henderson et al. |
| 5,633,316 A | 5/1997 | Gartner et al. |
| 5,981,070 A | 11/1999 | Ishizaki et al. |

FOREIGN PATENT DOCUMENTS

| EP | 0 417 761 A2 | 3/1991 |
| EP | 0 463 388 A1 | 1/1992 |
| EP | 0 496 594 A2 | 7/1992 |
| EP | 0 629 411 A1 | 12/1994 |
| EP | 0 695 763 A1 | 2/1996 |
| EP | 0 780 424 A1 | 6/1997 |
| EP | 0 789 047 A1 | 8/1997 |
| EP | 0 812 873 A1 | 12/1997 |
| JP | 51-136588 A | 11/1976 |
| JP | 52-117393 A | 10/1977 |
| JP | 58-180233 A | 10/1983 |
| JP | 61-16903 A | 1/1986 |
| JP | 61-211305 A | 9/1986 |
| JP | 2-227435 A | 9/1990 |
| JP | 3-501494 T | 4/1991 |
| JP | 3-152104 A | 6/1991 |
| JP | 4-41532 A | 2/1992 |
| JP | 4-214734 A | 8/1992 |
| JP | 4-227934 A | 8/1992 |
| JP | 5-43610 A | 2/1993 |
| JP | 5-508425 T | 11/1993 |
| JP | 6-510551 T | 11/1994 |
| JP | 7-88171 A | 4/1995 |
| WO | WO91/17200 | 11/1991 |
| WO | WO96/13542 | 5/1996 |
| WO | WO97/03114 A1 | 1/1997 |

*Primary Examiner*—Edward J. Cain

(57) ABSTRACT

The invention provides: a water-absorbent resin granule-containing composition with resolution of various problems, as caused by water-absorbent resin fine powders, and with high granulation strength, and with no physical property deterioration due to granulation, and, if anything, with improvement of the absorption capacity under a load by granulation; and a process for producing the above granule. A water-absorbent resin primary particle and a water-absorbent resin granule are separately surface-crosslinked and then mixed, or mixed and then surface-crosslinked. The granulation is carried out by mixing a preheated aqueous liquid and a water-absorbent resin powder at a high speed or by supplying a water-absorbent resin powder downstream of an aqueous liquid with a continuous extrusion mixer.

21 Claims, 11 Drawing Sheets

WATER-ABSORBENT RESIN GRANULE-CONTAINING COMPOSITION AND PRODUCTION PROCESS FOR WATER-ABSORBENT RESIN GRANULE

This application is a division of, and claims the benefit under 35 U.S.C. § 120 of, U.S. patent application Ser. No. 09/649,418 filed Aug. 26, 2000 now U.S. Pat. No. 6,458, 921, which was a continuation of, and claimed the benefit under 35 U.S.C. § 120 of, U.S. patent application Ser. No. 09/093,476 filed Jun. 9, 1998 (now U.S. Pat. No. 6,228,930).

BACKGROUND OF THE INVENTION

A. Technical Field

The present invention relates to a water-absorbent resin composition as favorably used for sanitary materials such as paper diapers (disposable diapers), sanitary napkins, and so-called incontinence pads. More specifically, the invention relates to: a water-absorbent resin composition containing a water-absorbent resin granule which is obtained by mixing a water-absorbent resin powder with an aqueous liquid and has high granulation strength and high absorption capacity under a load; and a process for producing the above granule.

B. Background Art

In recent years, water-absorbent resins are widely utilized as constituents of sanitary materials, such as paper diapers, sanitary napkins, and so-called incontinence pads, for the purpose of allowing the water-absorbent resins to absorb body fluids.

As to the above-mentioned water-absorbent resins, the following materials are, for example, known: crosslinked matters of partially neutralized polyacrylic acids, hydrolysates of starch-acrylic acid graft polymers, saponified products of vinyl acetate-acrylic ester copolymers, hydrolysates of acrylonitrile copolymers or those of acrylamide copolymers, or crosslinked matters of these copolymers, and crosslinked matters of cationic monomers.

It is said that the above-mentioned water-absorbent resins should be excellent in the following properties: the water absorption capacity, the water absorption speed, the liquid permeability, the gel strength of hydrogel, the suction power to suck up water from a base material containing an aqueous liquid, and so on, upon contact with an aqueous liquid such as a body fluid. However, relations between these properties do not necessarily display positive correlations. For example, as the absorption capacity increases, some other properties such as liquid permeability, gel strength, and absorption speed deteriorate.

As to a method for improving the above-mentioned water-absorption properties of a water-absorbent resin in good balance, an art in which the neighborhood of the surface of the water-absorbent resin is crosslinked is known, and various methods have been disclosed so far, and many crosslinking agents and conditions have been proposed.

For example, methods are known in each of which the following are used as crosslinking agents: polyhydric alcohols (JP-A-58-180233 and JP-A-61-016903); polyglycidyl compounds, polyaziridine compounds, polyamine compounds, or polyisocyanate compounds (JP-A-59-189103); glyoxal (JP-A-52-117393); polyvalent metals (JP-A-51-136588, JP-A-61-257235 and JP-A-62-007745); silane coupling agents (JP-A-61-211305, JP-A-61-252212, and JP-A-61-264006); alkylene carbonates (DE 4020780).

In addition, as to the crosslinking conditions, other methods are also known in which the following are allowed to be present during a crosslinking reaction: inert inorganic powders (JP-A-60-163956 and JP-A-60-255814); specific dihydric alcohols (JP-A-01-292004); water along with ether compounds (JP-A-02-153903); alkylene oxide adducts of monohydric alcohols, or organic acid salts, or lactams (EP 555692).

On the other hand, generally, as to a water-absorbent resin, it is preferable that the content therein of a powder with a particle diameter of not larger than 150 μm (i.e. fine powder) is as low as possible. The fine powder clogs even in absorbent articles such as diapers and therefore lowers the liquid permeability. In addition, there are problems in that the fine powder is lost as dust when handled, and further in that the properties such as absorption capacity under a load are difficult to improve even if the fine powder is treated by the above-mentioned surface-crosslinking. Thus, a water-absorbent resin containing only a small amount of fine powder is desirable.

Conventional known methods for producing the water-absorbent resin containing only a small amount of fine powder are, for example, as follows: (1) a method comprising adjustment of a particle size by an optimization of the degree of polymerization or pulverization; and (2) a method comprising classification and removal of the formed fine powder with a sieve or a gas current (U.S. Pat. No. 4,973, 632).

However, method (1) above gives a large amount of fine powder (ten and several percent to tens of percent) in production process steps. In addition, the abolition of the fine powder as produced in method (2) above results in the much lowering of yields and the disadvantage in the abolition cost.

Thus, various proposals have been made to resolve the above-mentioned problems by granulating or regenerating the fine powder as inevitably formed in production processes for water-absorbent resins.

For example, EP 0463388A, U.S. Pat. Nos. 4,950,692 and 4,970,267, EP 0417761A, and EP 0496594A propose methods (as means other than granulation) for regenerating the fine powder as large particles by pulverizing and then drying a gel which is formed by mixing the fine powder with water or a hydrogel. In addition, EP 0644224 proposes a granulation method comprising the step of carrying out granulation by adding an aqueous solution of a water-soluble or water-dispersible polymer to a water-absorbent resin in the presence of an insoluble inorganic fine powder such that the water content of the resultant granule can fall in the range of 30 to 70% by weight. U.S. Pat. No. 5,002,986, EP 0318989B, U.S. Pat. Nos. 5,248,709, 4,123,397, 4,734,478, and 5,369,148 propose methods for increasing the average particle diameter of the fine powder to some hundreds of micrometers by granulating the fine powder alone of about 150 micrometers to some tens of micrometers or a powdery mixture thereof with larger particles by using a binder such as an aqueous liquid in an amount of several percent to twenty and several percent of the powder.

However, it has been difficult to uniformly add an aqueous liquid to a water-absorbent resin fine powder because its absorption speed is fast due to its large surface area. In addition, there are problems in that the use of an insoluble inorganic fine powder as a mixing-promotor, generally, results not only in the disadvantage of cost, but also in the formation of dust from the insoluble inorganic fine powder or in the deterioration of the granulation strength or the physical properties.

The present inventors found that there are problems in that even if water-absorbent resin powders are granulated using conventional granulating machines or methods, excellent absorption properties as expected cannot be maintained in final products, probably, due to destruction of granulation in conveyance steps of the water-absorbent resins or in processing steps to the final products (for example, paper diapers).

Furthermore, the inventors found that there might been seen physical property deteriorations, such as lowering of the absorption speed, increasing of water-soluble components as impurities, or lowering of the absorption capacity under a load, as a result of regeneration of fine powders due to the above-mentioned destruction of granulation, and further that, on the other hand, the inherent properties of the water-absorbent resin deteriorate when a granulation strength is increased by increasing the amount of an aqueous liquid, which is a binder, for the purpose of avoiding the destruction of granulation.

For example, fluidized-bed type mixers (EP 0318989) or high-speed stirring type mixers (U.S. Pat. No. 5,140,076), as conventionally used for granulation, provide inferior results in that the amount of an aqueous liquid as added to a water-absorbent resin powder is only several % up to at most 30%, and that it is very difficult to continuously and stably make granulation with the amount of the addition over 30%.

Furthermore, as to the conventional granulation methods, in the case where the amount of the addition of the aqueous liquid is larger than 30%, the mixing of the aqueous liquid and the water-absorbent resin powder is extremely non-uniform, and the physical-property deterioration or particle destruction occurs due to the non-uniform addition of the aqueous liquid. Thus, there is a limitation in the amount of the addition of the aqueous liquid for improving the granulation strength.

In addition, by the present inventors' study, it was found that: mixers with great kneading power, as conventionally used as means other than granulation, such as shearing mixers (EP 0417761) and Nauta type mixers, relatively facilitate the addition of the aqueous liquid, but provide inferior results in that a mixture resultant from the addition of the aqueous liquid does not form a granule, but merely forms a united large mass of a gel, and that the water-absorbent resin itself is deteriorated due to the shearing force of the mixers.

In addition, the present inventors further found that conventional processes, such as a process comprising granulation after crosslinking the surface neighborhood of a water-absorbent resin and a process comprising the simultaneous steps of the granulation and the surface-crosslinking of the water-absorbent resin, inevitably involve surface-crosslinking fracture due to the granulation, in other words, that water-absorbent resin compositions as obtained by the conventional granulation processes can bear only a low load of at most about 20 g/cm$^2$ because of the fracture due to the granulation and display only a low absorption capacity of ten and several g/g under a high load of 50 g/cm$^2$.

In addition, the present inventors further found that a water-absorbent resin primary particle alone, as obtained by removing the fine powder by classification, is not only economically disadvantageous because of the removal of the fine powder, but also slow in water absorption speed because of its small surface area, and further that a granule particle alone involves complicated process steps and is inferior because of factors such as gel fracture.

SUMMARY OF THE INVENTION

A. Objects of the Invention

Thus, the present invention has been made considering the above-mentioned prior-art problems, and has an object to provide a water-absorbent resin granule and a composition containing it with resolution of the above-mentioned various prior-art problems, as caused by the water-absorbent resin fine powder, and with high granulation strength, and with no physical property deterioration due to granulation, and, if anything, with improvement of the absorption capacity under a load by granulation.

B. Disclosure of the Invention

The present inventors made investigations in order to resolve the above-mentioned problems, as caused by the water-absorbent resin fine powder, and to increase the granulation strength of the water-absorbent resin, and to remove the physical property deterioration which might be caused by granulation, and further to obtain a water-absorbent resin granule with physical properties better than conventional ones by aggressively using the fine powder. Consequently, the inventors accomplished the present invention by finding that a water-absorbent resin granule with excellent properties can be produced whenever the below-mentioned constitutions are satisfied in a process for producing a water-absorbent resin granule by mixing a water-absorbent resin with an aqueous liquid, and further that it is also necessary to contrive the timing of the surface-crosslinking.

Thus, to resolve the above problems, a water-absorbent resin composition, according to an embodiment of the present invention, comprises a product by surface-crosslinking a mixture of a water-absorbent resin primary particle and a water-absorbent resin granule.

A water-absorbent resin composition, according to another embodiment of the present invention, comprises a mixture of a surface-crosslinked product of a water-absorbent resin primary particle and a surface-crosslinked product of a water-absorbent resin granule.

A water-absorbent resin composition, according to further another embodiment of the present invention, comprises a mixture of a water-absorbent resin primary particle and a water-absorbent resin granule and has an absorption capacity of at least 25 g/g for a physiological salt solution under a load of 50 g/cm$^2$.

A process for producing a water-absorbent resin composition, according to an embodiment of the present invention, comprises the step of adding a crosslinking agent to a mixture of a water-absorbent resin primary particle and a water-absorbent resin granule, thus crosslinking the surface neighborhood of the mixture.

A process for producing a water-absorbent resin composition, according to another embodiment of the present invention, comprises the step of mixing a surface-crosslinked product of a water-absorbent resin primary particle and a surface-crosslinked product of a water-absorbent resin granule.

A process for producing a water-absorbent resin granule, according to an embodiment of the present invention, comprises the step of mixing a water-absorbent resin powder with a preheated aqueous liquid at a high speed, thus obtaining a water-absorbent resin granule.

A process for producing a water-absorbent resin granule, according to another embodiment of the present invention, comprises the steps of: supplying a water-absorbent resin powder and an aqueous liquid into a continuous extrusion mixer having a plurality of supplying-inlets along an arrangement of stirring-members, wherein the water-absorbent resin powder is supplied downstream of the aqueous liquid; and mixing the water-absorbent resin powder and the aqueous liquid in the continuous extrusion mixer, thus continuously granulating the water-absorbent resin powder (hereinafter, this process might be referred to as "continuous granulation process" or "process for continuously granulating").

These and other objects and the advantages of the present invention will be more fully apparent from the following detailed disclosure.

DETAILED DESCRIPTION OF THE INVENTION

Figure 1:
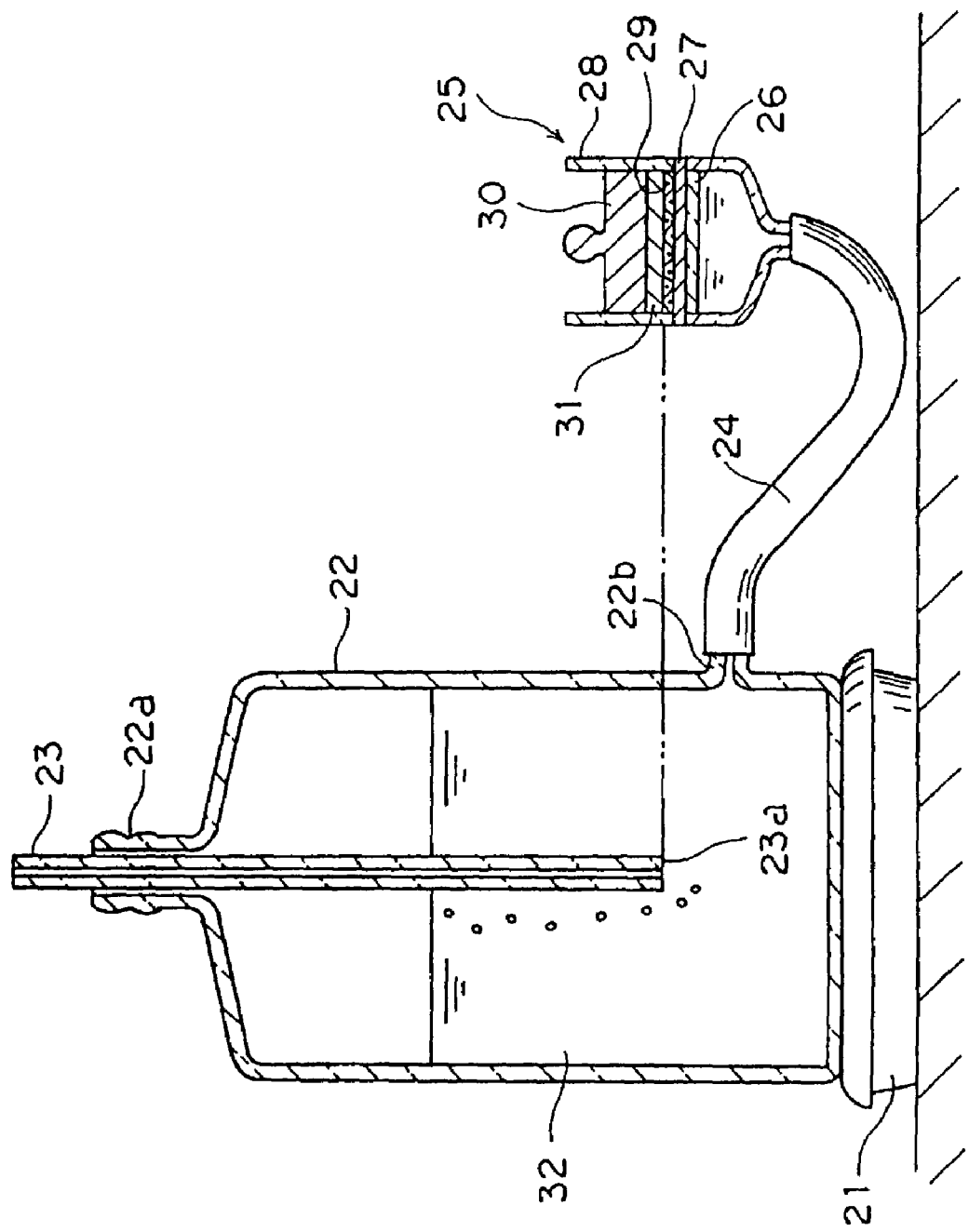
FIG. 1 illustrates a measurement apparatus for the water absorption capacity under a load as used in the present invention.

Hereinafter, the present invention is explained in detail.

First, an explanation is made on a process for producing a water-absorbent resin powder which is used in the present invention.

As to the water-absorbent resin powder as used in the present invention, a wide range of conventional water-absorbent resin powders are available, and among them, particularly, those which possess a carboxyl group are preferable. The usable water-absorbent resin powder is a powder of conventional water-absorbent resins which are typically obtained by polymerizing and crosslinking hydrophilic monomers comprising a major proportion of either or both of acrylic acid and its salt, and form a hydrogel in water due to the absorption of as large an amount of water as 50 to 3,000 times of themselves. In addition, as to the above-mentioned water-absorbent resins as used, the water-soluble content therein is not larger than 25% by weight, preferably, not larger than 15% by weight, and more preferably, not larger than 10% by weight.

Examples of the acrylic acid salt, as described above, include alkaline metal salts, ammonium salt, and amine salts of acrylic acid. The above-mentioned water-absorbent resin preferably comprises acrylic acid of 10 to 40 mol % and acrylic acid salt of 60 to 90 mol % (wherein their total is 100 mol %). The neutralization of acrylic acid or its polymer can be performed in the monomer form, or in the middle of polymerization, or after polymerization.

When the water-absorbent resin is obtained by polymerizing the hydrophilic monomers comprising a major proportion of either or both of acrylic acid and its salt, the hydrophilic monomers are permitted to include monomers other than acrylic acid along with the acrylic acid or its salt.

The monomers other than acrylic acid are not especially limited, but examples thereof include: anionic unsaturated monomers, such as methacrylic acid, maleic acid, vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid, and their salts; nonionic unsaturated monomers containing hydrophilic groups, such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine; and cationic unsaturated monomers such as N,N-dimethylaminoethyl (meth)acrylate, N,N-diethylaminoethyl (meth)acrylate, N,N-dimethylaminopropyl (meth)acrylate, N,N-dimethylaminopropyl (meth)acrylamide, and their quaternary salts. These monomers may be used either alone or in combinations of at least two thereof fitly.

In the present invention, when using the monomers other than acrylic acid, the proportion of the monomers other than acrylic acid is preferably not higher than 30 mol %, more preferably, not higher than 10 mol %, of the total amount of acrylic acid and its salt as are used as the main components.

When the hydrophilic monomers comprising a major proportion of either or both of acrylic acid and its salt are polymerized to give the water-absorbent resin as used in the present invention, bulk polymerization or precipitation polymerization can be performed, but it is preferable to perform aqueous solution polymerization or reversed-phase suspension polymerization using an aqueous solution of the above-mentioned hydrophilic monomers in view of the good performance achievement or the easiness in controlling the polymerization.

Incidentally, where the above-mentioned hydrophilic monomers are used in the form of an aqueous solution thereof (hereinafter referred to as "aqueous monomer solution"), although not specifically limited, the concentration of the monomers in the aqueous monomer solution is preferably in the range of 10 to 70% by weight, more preferably, 20 to 40% by weight. In addition, in the case of the above-mentioned aqueous solution polymerization or reversed-phase suspension polymerization, solvents other than water may be used together with water if need arises, and the solvents used together is not specifically limited.

When the above-mentioned polymerization is initiated, the following radical polymerization initiators, for example, can be used: potassium persulfate, ammonium persulfate, sodium persulfate, t-butyl hydroperoxide, hydrogen peroxide, and 2,2'-azobis(2-aminodipropane) dihydrochloride.

Furthermore, it is possible to use a redox initiator as formed by combining with the polymerization initiator a reducing agent which accelerates the decomposition of the initiator. Examples of the reducing agent include: sulfurous acid or (bi)sulfites such as sodium sulfite and sodium hydrogen sulfite; L-ascorbic acid (or its salts); reducible metals (or its salts) such as ferrous salts; and amines. However, the reducing agent is not specifically limited.

The amount of the polymerization initiator as used is not specifically limited, but is usually in the range of 0.001 to 2 mol %, preferably 0.01 to 0.5 mol %, of the monomer. In the case where the amount of the initiator is smaller than 0.001 mol %, the amount of unreacted monomers increases, so the amount of residual monomers in the resultant water-absorbent resin unfavorably increases. On the other hand, in the case where the amount of the initiator as used exceeds 2 mol %, the water-soluble content in the resultant water-absorbent resin unfavorably increases, and this is also unpreferable.

In addition, instead of using the polymerization initiator, irradiation of active energy rays such as radiations, electron rays, and ultraviolet rays to the reaction system may be utilized for the polymerization reaction. Incidentally, although not specifically limited, the reaction temperature in the above-mentioned polymerization reaction is preferably in the range of 20 to 90° C. The reaction period of time is not specifically limited, either, and it may be determined fitly depending on factors such as the type of the hydrophilic monomer or polymerization initiator or the reaction temperature.

The water-absorbent resin, used in the present invention, may be a self-crosslinking type which does not need any crosslinking agent, but preferable ones are those which are obtained by a copolymerization or reaction with an internal crosslinking agent having, per molecule thereof, at least two polymerizable unsaturated groups or at least two reactive groups.

Specified examples of the internal crosslinking agent include N,N-methylenebis(meth)acrylamide, (poly)ethylene glycol (meth)acrylate, (poly)propylene glycol di(meth)acrylate, trimethylolpropane tri(meth)acrylate, glycerol tri(meth)acrylate, glycerol acrylate methacrylate, ethylene oxide-denatured trimethylolpropane tri(meth)acrylate, pentaerythritol hexa(meth)acrylate, triallyl cyanurate, triallyl isocyanurate, triallyl phosphate, triallylamine, poly (meth)allyloxyalkanes, (poly)ethylene glycol diglycidyl ether, glycerol diglycidyl ether, ethylene glycol, polyethylene glycol, propylene glycol, glycerin, pentaerythritol, ethylenediamine, ethylene carbonate, propylene carbonate, polyethylenimine, glycidyl (meth)acrylate.

These internal crosslinking agents may be used either alone or in combinations of at least two thereof fitly. In addition, these internal crosslinking agents may be added to the reaction system either collectively or separately. In the case of using at least two internal crosslinking agents, it is preferable to never fail to use a compound possessing at least two polymerizable unsaturated groups under consideration of the absorption properties of the resultant water-absorbent resin. The amount of the internal crosslinking agent, as used, is preferably in the range of 0.005 to 2 mol %, more preferably, 0.01 to 1 mol %, of the above-mentioned monomer component. In the case where the amount of the above-mentioned internal crosslinking agent as used is smaller than 0.005 mol % or larger than 2 mol %, a water-absorbent resin with desired absorption properties might not be obtained.

When a crosslinked structure is introduced into the water-absorbent resin using the internal crosslinking agent, the internal crosslinking agent may be added into the reaction system during or after the polymerization of the monomer component, or after the polymerization and the neutralization of the monomer component.

When carrying out the polymerization, the following materials may be added to the reaction system: inert gases such as nitrogen; foaming agents such as (hydrogen) carbonates, carbon dioxide, azo compounds, and inert organic solvents; hydrophilic polymers such as starch-cellulose, derivatives of starch-cellulose, polyvinyl alcohol, poly-acrylic acid (or its salts), and crosslinked polyacrylic acid (or its salts); surface-active agents; and chain transfer agents such as hypophosphorous acid (or its salts).

In the case where the polymer as obtained by the above polymerization reaction is gelatinous, this gelatinous polymer is dried and then, if necessary, pulverized, thus obtaining the water-absorbent resin powder as used in the present invention.

Next, in the present invention, the water-absorbent resin primary particle and the water-absorbent resin granule are obtained using the resultant water-absorbent resin powder.

The water-absorbent resin primary particle, used as one of the raw materials in the present invention, is a substantially ungranulated water-absorbent resin powder, and is a single particle or the like which not a little force is needed for breaking, for example, which does not break due to classification or conveyance operations. It is enough that the water-absorbent resin primary particle in the present invention is particulate to such a degree that the object of the present invention can be achieved, and the size of the water-absorbent resin primary particle is not especially limited. If the water absorption properties of the resultant water-absorbent resin composition is considered, the average particle diameter of the water-absorbent resin primary particle is in the range of, preferably, 150 to 800 μm, more preferably, 200 to 600 μm, and further preferably the water-absorbent resin primary particle contains substantially no particle larger than 1,000 μm. In the case where the average particle diameter of the water-absorbent resin primary particle is smaller than 150 μm, the liquid permeability of the resultant water-absorbent resin composition tends to be poor, and in the case where the average particle diameter of the water-absorbent resin primary particle is larger than 800 μm, the absorption speed tends to be low. In addition, in the case where the particle diameter of the water-absorbent resin primary particle is too large, when used for sanitary materials the resultant water-absorbent resin composition might give a physical feeling of something foreign to users of the sanitary materials. Thus, the water-absorbent resin primary particle has a particle diameter of, preferably, 850 to 105 μm, more preferably, 850 to 150 μm, particularly preferably, 710 to 150 μm.

In addition, it is enough that the water-absorbent resin granule, used as the other raw material in the present invention, is particulate to such a degree that the object of the present invention can be achieved, and the size of the water-absorbent resin primary particle is not especially limited. If the water absorption properties of the resultant water-absorbent resin composition is considered, the average particle diameter of the granule is in the range of, preferably, 150 to 800 μm, more preferably, 200 to 600 μm, and further preferably, the granule contains substantially no particle larger than 1,000 μm. In the case where the average particle diameter of the granule is smaller than 150 μm, the liquid permeability of the resultant water-absorbent resin composition tends to be poor, and in the case where the average particle diameter of the granule is larger than 800 μm, the absorption speed tends to be low. In addition, in the case where the particle diameter of the granule is too large, when used as an absorbing agent of sanitary materials the resultant water-absorbent resin composition might give a physical feeling of something foreign to users of the sanitary materials.

The water-absorbent resin powder, as used as a raw material for the granule in the present invention, may be any form of the following: only a fine powder of a water-absorbent resin (for example, consisting of particles having a particle diameter of not larger than 150 µm); a mixture (for example, particles having a particle diameter of not larger than 850 µm as a whole, including particles of not larger than 150 µm) of the fine powder and larger particles therethan (for example, particles having a particle diameter of not smaller than 150 µm); a fine-powder-free water-absorbent resin (for example, consisting of particles having a particle diameter of 150 µm to 850 µm both inclusive). Furthermore, the usable fine powder may be a classified and removed one from mixtures in production steps, or, for the purpose of attaining a high absorption speed, the usable fine powder may be such as obtained alone by intentional adjustment of pulverization or polymerization conditions.

Among these water-absorbent resin powders, the fine powder of the water-absorbent resin is preferably used as a raw material for the water-absorbent resin granule. The average particle diameter of the fine powder is preferably in the range of 150 to 10 µm, and the content of particles with a particle diameter of substantially not larger than 150 µm in the fine powder is preferably not lower than 70% by weight, and more preferably, not lower than 90% by weight. As to the shape of the fine powder, from the viewpoint of the granulation strength, an irregular shape as formed by aqueous solution polymerization is preferred to a spherical shape as formed by reversed-phase suspension polymerization. Furthermore, fine powders which have not yet been subjected to surface-crosslinking treatment is more preferable. Furthermore, it is preferable that the fine powder of the water-absorbent resin is a product from classification of the water-absorbent resin primary particle.

Figure 8:
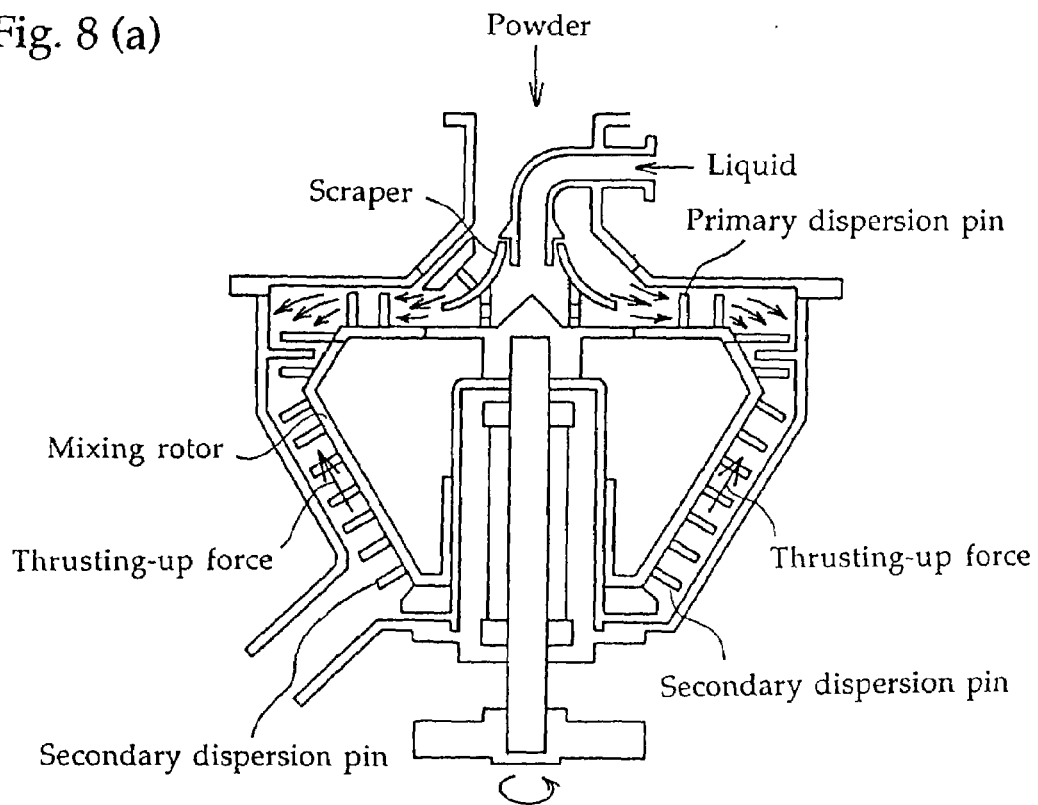
FIG. 8 illustrates examples of granulators as used in the present invention process for producing a water-absorbent resin granule.
Figure 8:
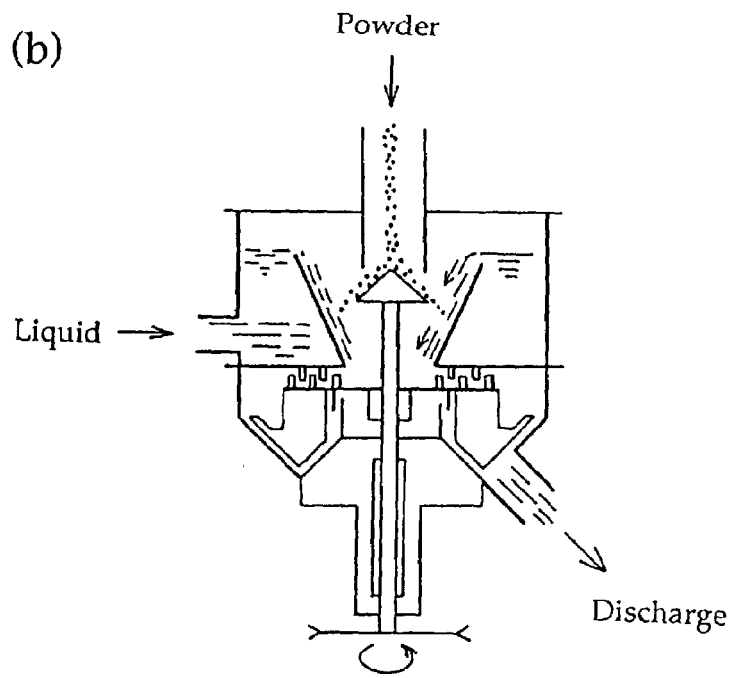
Figure 8:
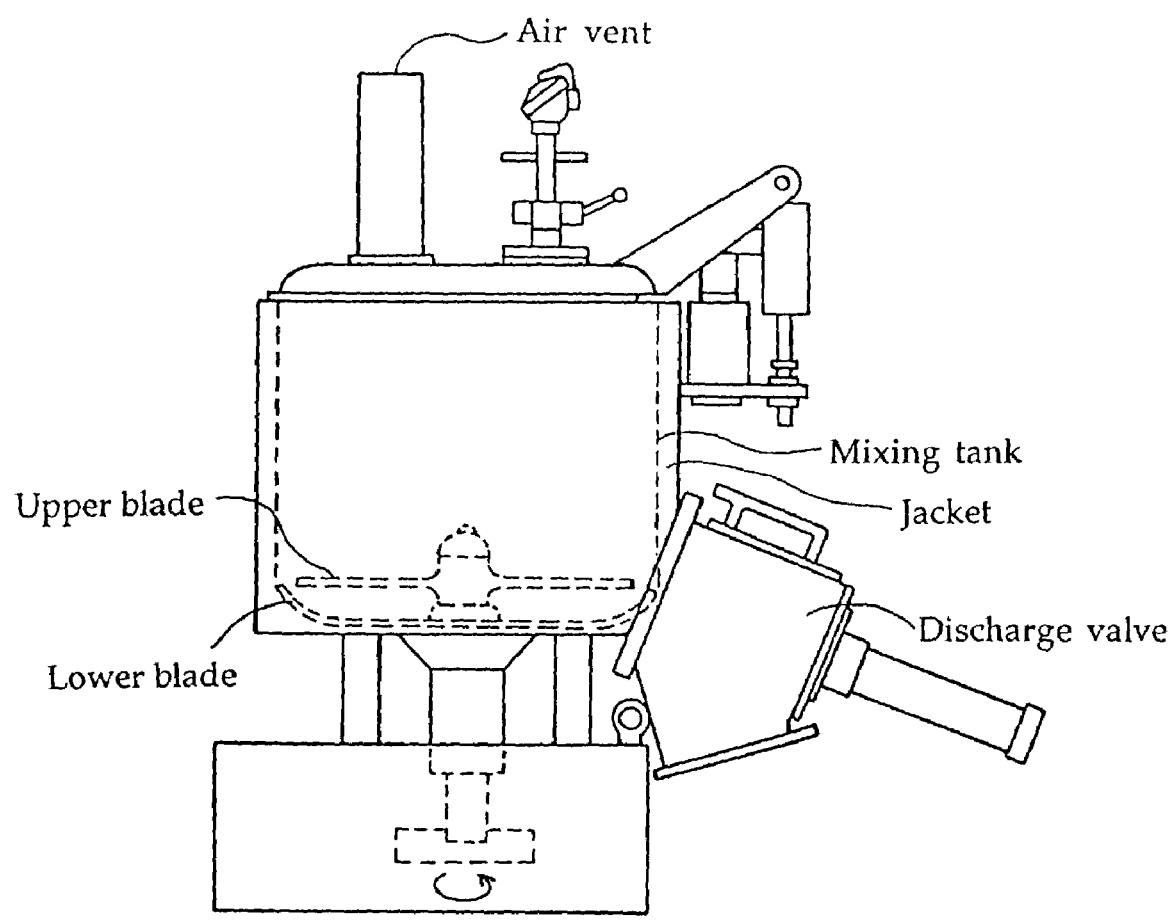
Figure 8:
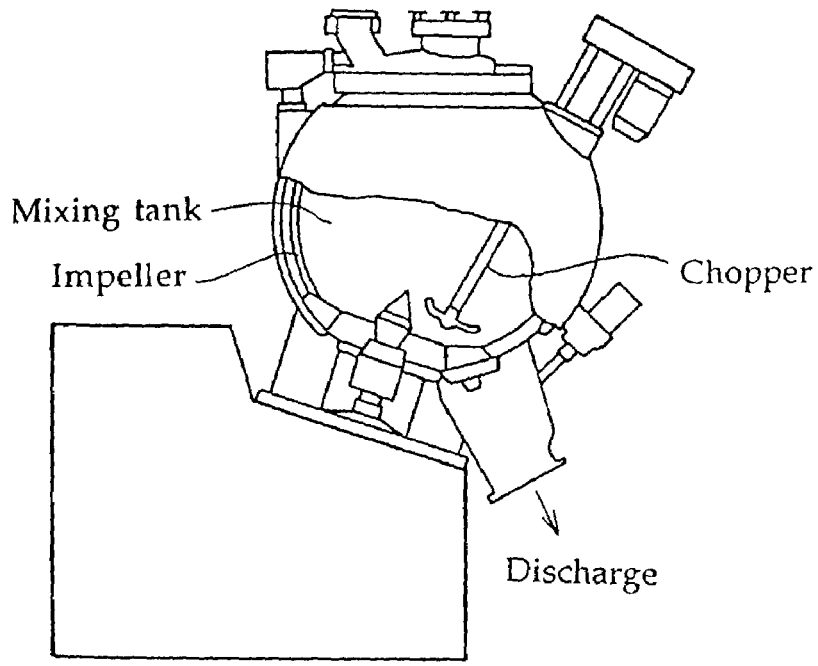
Figure 8:
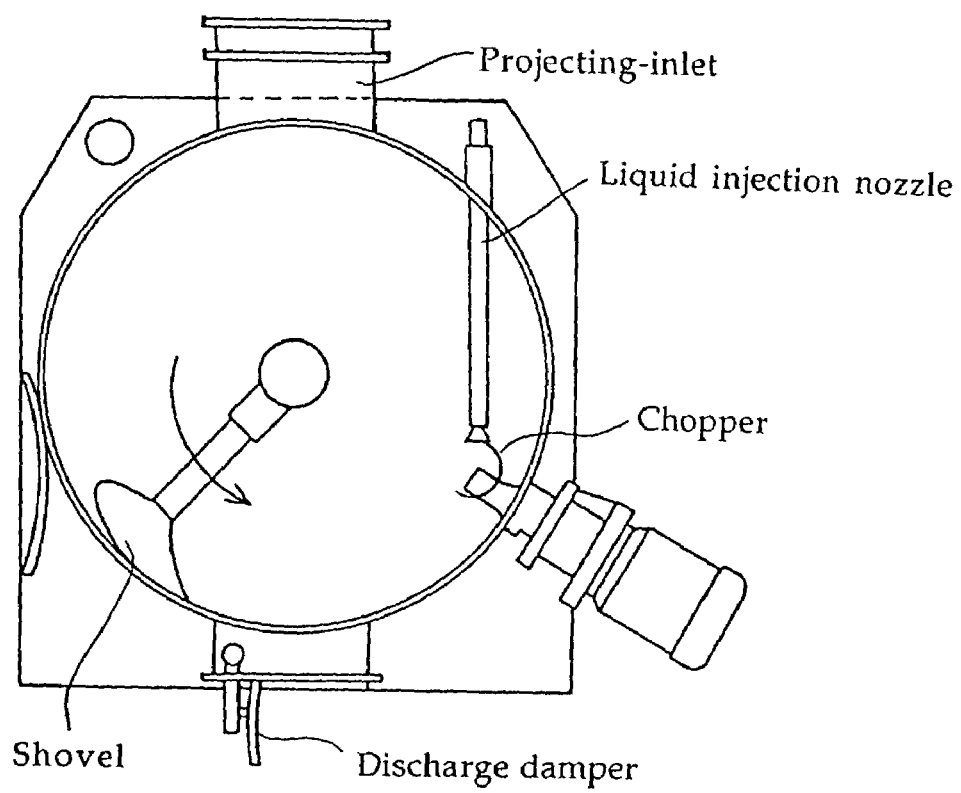
Figure 8:
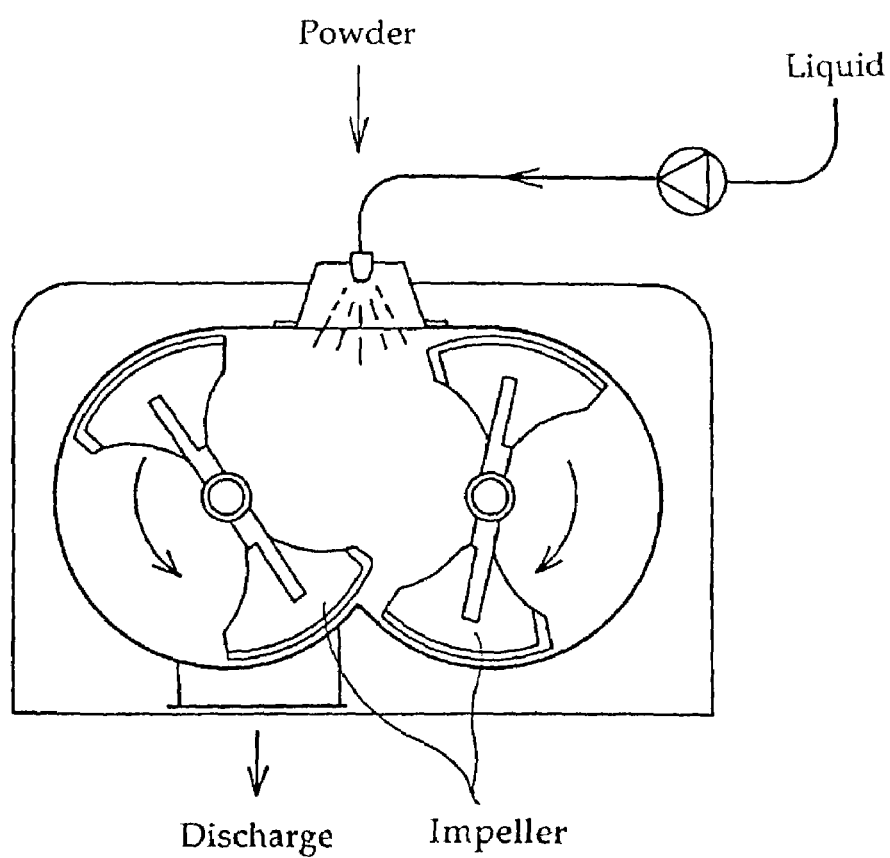

Various polymers, such as polyanion (e.g., polyethylenimine) and nonion, and polyhydric alcohols, such as glycerol, can also be used as granulation binders for obtaining the water-absorbent resin granule in the present invention, but, in view of physical properties or safety, it is preferable that the granulation is carried out using a binder comprising an aqueous liquid as an essential component. The method for obtaining the water-absorbent resin granule using the aqueous liquid in the present invention is not especially limited, but examples thereof include tumbling granulation methods, compression type granulation methods, stirring type granulation methods, extrusion granulation methods, pulverization type granulation methods, fluidized-bed granulation methods, spray drying granulation methods. Among these granulation methods, the stirring type ones can be used most conveniently. The apparatus, as used to perform such methods, may be either a continuous or batch type, each including a tower type and a sideways type. Examples of the tower type continuous granulator include Spiral Pin Mixer made by Pacific Machinery & Engineering Co., Ltd. (FIG. 8(a)) and Flow Jet Mixer made by Funken Powtex (FIG. 8(b)). Examples of the sideways type continuous granulator include Annular Layer Mixer made by Draiswerke GmbH. Examples of the tower type batch granulator include Henschel mixer made by Mitsui Kozan K. K. (FIG. 8(c)) and Turbo Sphere Mixer made by Moritz (FIG. 8(d)). Examples of the sideways type batch granulator include Lödige Mixer made by Gebrüder Lödige Maschinenbau GmbH (FIG. 8(e)) and Gericke Multi-Flux Mixer made by Gericke GmbH (FIG. 8(f)).

The amount of the aqueous liquid, as used, is preferably not smaller than about 1 part by weight, more preferably, in the range of about 2 to about 280 parts by weight, per 100 parts by weight of the water-absorbent resin powder. In the case where the amount of the aqueous liquid, as used, is too small, granulation failures easily occur, and therefore the object of the present invention might not be achieved.

Especially, in the case where as large an amount as 80 to 280 parts by weight of the aqueous liquid is mixed to further improve the granulation strength or the absorption capacity under a load, a granulation method as preferably used among the above-mentioned ones in view of good mixing-ability is either or both of (a) a method in which the aqueous liquid is preheated prior to mixing and then the granulation is carried out, and (b) a method in which the granulation is carried out using a specific mixer.

In the present invention, specifically, a preferable water-absorbent resin granule is either or both of (a) a granule as obtained by a process comprising the step of mixing a preheated aqueous liquid into a water-absorbent resin powder at a high speed, and (b) a granule as obtained by a process in which a water-absorbent resin powder and an aqueous liquid are mixed by an adding and mixing method using a high-speed-stirring type continuous extrusion mixer including a plurality of impellers around a rotary shaft in a fixed cylinder, wherein the mixer is operated such that the water-absorbent resin is supplied into an area where a plurality of first impellers, as shaped to generate an extrusion thrust, are arranged, and that the aqueous liquid is supplied into an area where a plurality of second impellers, as shaped to generate an extrusion thrust smaller than that by the first impellers, are arranged on the discharge side of the first impellers, thus mixing the water-absorbent resin and the aqueous liquid.

The aforementioned granulation is known as one of conventional methods for combining a plurality of water-absorbent resin powders with each other to form a particle, and water or the aqueous liquid is often used as the binder in those conventional methods. However, even if high-speed agitation type mixers (preceding U.S. Pat. Nos. 5,002,986 and 4,734,478), specific spray continuous granulators (U.S. Pat. No. 5,369,148), fluidized beds (EP 0318989), or the like are used in those conventional methods, the amount of water as added was merely at most around 30 parts by weight, even including non-uniform aggregates, per 100 parts by weight of the water-absorbent resin in view of the mixing-ability of water. In the case where the amount of the aqueous liquid is small, the resultant granulation strength is insufficient, so the object of the present invention is difficult to achieve.

In addition, a method in which mixing-promotors such as insoluble inorganic powders or water-soluble polymers are used to improve the mixing-ability of water in the granulation (EP 064424) still gives non-uniform mixing, and further, the use of the mixing-promotors rather deteriorates the granulation strength or the physical properties.

A process in which a hydrogel is produced from a water-absorbent resin and then kneaded and pulverized in sequence was also proposed as another process not according to the process in which a particulate water-absorbent resin granule of a plurality of particles is directly obtained by mixing a water-absorbent resin powder with an aqueous liquid. However, such a prior art process has problems in that, for example, in the case where a shearing mixer (EP 0417761) or a Nauta type mixer is used to mix the above-mentioned fine powder with the aqueous liquid, even the addition and mixing of water over 100 parts by weight is possible due to the strong shearing force of the mixer, but the powder is merely united and therefore is not particulated, and further, in the case where the kneading is carried out with too strong force, the water-absorbent resin is deteriorated due to the shearing force of such kneading.

Accordingly, for improving the granulation strength of the water-absorbent resin granule without deteriorating the physical properties thereof, it is important to set the amount of the aqueous liquid, as added, relative to the water-absorbent resin within a predetermined range and further to directly obtain a particulate water-absorbent resin granule. Incidentally, "to directly obtain a particulate water-absorbent resin granule" is not a process in which a united gel is obtained by, for example, kneading and the resultant huge gel is then pulverized or finely divided, but to obtain a particulate water-absorbent resin with a specific particle size by aggregating a plurality of water-absorbent resin powders.

In addition, there is also a proposed process in which a water-absorbent resin powder and an aqueous liquid are mixed by kneading to form an amorphous gel, and the resultant gel is then pulverized. However, such a prior art process has problems in that in the case where a shearing mixer (EP 0417761) or a Nauta type mixer (U.S. Pat. No. 4,950,692) is used to mix the water-absorbent resin fine powder with the aqueous liquid, the water-absorbent resin is deteriorated due to the strong shearing force of the mixer. Accordingly, for improving the granulation strength or the physical properties, it is important to directly obtain a water-absorbent resin granule by making a granulation in a short time by mixing the water-absorbent resin powder with the aqueous liquid.

Incidentally, "to directly obtain a water-absorbent resin granule" is not a process in which a united gel mass is obtained by, for example, kneading and the resultant huge gel mass is then pulverized or finely divided, but to obtain a particulate water-absorbent resin granule with a specific particle size by aggregating a plurality of water-absorbent resin powders.

Because the heated aqueous liquid is used, it is possible to mix a water-absorbent resin powder with an aqueous liquid homogeneously without kneading them and further without using any mixing-promotor which causes physical property deterioration. In addition, because the heated aqueous liquid is used, a particulate aggregate with an appropriate particle size, as formed by aggregation of respective water-absorbent resin particles, that is, the water-absorbent resin granule favorable for the present invention, can be produced.

The formation of the granule can be confirmed by observing with an optical microscope a fact that a plurality of respective particles are aggregated to cohere with their particle shapes kept, or by observing a fact that respective particles swell as a plurality of discontinuous particles when absorbing a liquid.

In the present invention, it is further preferable to use either or both of (a) the foregoing method in which the aqueous liquid is preheated prior to mixing and then the granulation is carried out, and (b) the foregoing method in which the granulation is carried out using a specific mixer, because, for the first time, these methods can give a particulate water-absorbent resin granule, comprising substantially water and the fine powder, without using any mixing-promotor, as conventionally used for granulation, and without carrying out the gel pulverization as conventionally used as a means other than granulation.

Examples of the aqueous liquid, as used for the granulation, include water, aqueous solutions containing hydrophilic organic solvents as described hereinafter, and heated water containing a small amount of crosslinking agents. In this case, usable crosslinking agents include surface-crosslinking agents with types and amounts as described hereinafter. The joint use of the crosslinking agent with the aqueous liquid sometimes make it possible to decrease the water-soluble content or further improve the granulation strength.

Hereinafter, a further explanation is made on the method (a) above in which the aqueous liquid is preheated prior to mixing and then the granulation is carried out.

The heating temperature of the aqueous liquid is, usually, not lower than 40° C., preferably, not lower than 50° C., more preferably, not lower than 60° C., still more preferably, not lower than 70° C. The upper limit thereof is not higher than the boiling point of the aqueous liquid, and it is usually not higher than 100° C. because no remarkable change is made even above 100° C., while the boiling point may be variously controlled by adding salts or other solvents or changing factors such as pressure (decreasing or increasing the pressure).

Unless the aqueous liquid is heated in advance before mixing, the water-absorbent resin granule comprising a plurality of water-absorbent resin powders is difficult to obtain by a process in which the water-absorbent resin powder is mixed with the aqueous liquid, and consequently, it is impossible to control the particle diameter of the resultant water-absorbent resin granule, and in addition, in the case where the amount of the aqueous liquid as added is large, the resultant water-absorbent resin granule is a united large gelatinous one, and it is impossible to actually isolate and handle it as a granulated product, and furthermore, there are problems in that the water-absorbent resin itself is degraded due to cutting-off or twining of main chains as caused by the requirement of high mixing-power or by a kneaded state of the resultant gelatinous mass (incidentally, such problems can otherwise be solved by the below-mentioned granulation method (b) as well).

On the other hand, if a simple method of heating the aqueous liquid in advance before mixing is carried out, the water-absorbent resin granule comprising a plurality of water-absorbent resin powders can be obtained by mixing the water-absorbent resin powder with the aqueous liquid without needing any special mixer or any pulverizer to pulverize the united gelatinous substance separately. Incidentally, the water-absorbent resin granule, as referred to in the present invention, comprises a plurality of water-absorbent resin powders and has a particle diameter as the granule of not larger than 20 mm, preferably, in the range of 0.3 to 10 mm, and more preferably, 0.3 to 5 mm. In addition, the water-absorbent resin granule, as referred to in the present invention, is a generic name of water-containing or dry granules, and further, a product as obtained by drying the water-absorbent resin granule might otherwise be referred to as water-absorbent resin granule-dried matter with a water content of not more than 10% by weight.

For obtaining the water-absorbent resin granule to accomplish the object of the present invention, it is preferable to preheat the water-absorbent resin powder as well as the aqueous liquid. The heating temperature of the water-absorbent resin powder in the present invention is, usually, not lower than 40° C., preferably, not lower than 50° C., and, usually, not higher than 100° C. because no remarkable change is made even above 100° C.

In the present invention, the aqueous liquid to be mixed with the water-absorbent resin powder is not specifically limited, but examples of the aqueous liquid include water and aqueous liquids containing water-soluble salts or hydrophilic organic solvents. The water content in the aqueous liquid is preferably not less than 90% by weight, more preferably, not less than 99% by weight, still more preferably, in the range of 99 to 100% by weight, and particularly preferably, 100% by weight, from the viewpoint of factors such as physical properties, granulation strength, efficiency, safety, and production cost.

The amount of the aqueous liquid, as used, is, usually, not smaller than 1 part by weight, preferably, not smaller than 5 parts by weight, but, in view of granulation strength, preferably in the range of 80 to 280 parts by weight, per 100 parts by weight of the water-absorbent resin powder. In the case where the amount of the aqueous liquid as used exceeds 280 parts by weight, the resultant water-absorbent resin granule is difficult to actually handle as the granule, and further there are disadvantages from a viewpoint of the cost for drying. On the other hand, in the case where the amount of the aqueous liquid, as used, is smaller than 80 parts by weight, the granulation strength might be insufficient, and the resultant final product might therefore not be able to display excellent properties, and further there is a possibility that any granule could not be obtained due to non-uniform mixing.

The high-speed mixing of the heated aqueous liquid with the water-absorbent resin powder is preferable. The high-speed mixing denotes that the period of time for completion of mixing the aqueous liquid with the water-absorbent resin powder and formation of the water-absorbent resin granule is short. The period of time from the contact between the aqueous liquid and the water-absorbent resin powder till the formation of the water-absorbent resin granule, that is, the mixing period of time, is short. The mixing period of time is preferably not longer than 3 minutes, more preferably, not longer than 1 minute, and most preferably, in the range of 1 to 60 seconds.

In the case where the mixing period of time is long, it is difficult to homogeneously mix the aqueous liquid with the water-absorbent resin powder, resulting in a formation of a large aggregate, and consequently, it is impossible to obtain the water-absorbent resin granule which is an object of the present invention. Furthermore, in the case where the stirring is continued for a long time after the completion of the mixing, the water-absorbent resin might involve the deterioration thereof such as an increase of the water-soluble content and a decrease of the absorption capacity under a load.

If the above-mentioned high-speed mixing can be achieved, the mixer as used therefor is not specifically limited, but preferable ones are vessel-fixing type mixers, particularly, mechanical-stirring type mixers. Examples of thereof include Turbulizer (made by Hosokawa Mikron Co., Ltd.), Lödige Mixer (made by Gebrüder Lödige Maschinenbau GmbH), a mortar mixer (made by Nishi Nihon Shikenki K. K.), Henschel mixer (made by Mitsui Kozan K. K.), Turbo Sphere Mixer (made by Moritz), and Gericke Multi-Flux Mixer (made by Gericke GmbH). The mixer as used may be either a batch-type mixer or a continuous-type mixer.

Next, an explanation is made on the method (b) above in which the granulation is carried out using a specific mixer.

The specific mixer, as used in the method (b), is a continuous extrusion mixer as illustrated in JP-A-09-235378, and impellers as provided to this mixer comprise at least two kinds of impellers of different shapes, so the mixing is carried out in at least two agitation states. As a result, the water-absorbent resin powder is mixed with the heated aqueous liquid more efficiently, and further uniform mixing can be ensured.

In addition, the plurality of impellers in the continuous extrusion mixer, as illustrated in JP-A-09-235378, are, preferably, spirally arranged in sequence, whereby an extrusion thrust can sufficiently be ensured and further the water-absorbent resin powder or the composite thereof can smoothly be extruded. In addition, preferably, a plurality of first impellers and a plurality of second impellers are arranged in sequence around a rotary shaft in the above-mentioned continuous extrusion mixer, wherein the first impellers are set on the material-supplying side and shaped to generate an extrusion thrust, and the second impellers are set on the discharge side of the first impellers and shaped to generate an extrusion thrust smaller than that by the first impellers. Specifically, the first impellers give the water-absorbent resin powder and the heated aqueous liquid a sufficient extrusion thrust into the continuous extrusion mixer, and next, the second impellers reduce the extrusion thrust to smaller than that by the first impellers, so that the mixing-stirring time can sufficiently be obtained to sufficiently carry out the mixing. Therefore, the water-absorbent resin powder can be mixed with the (heated) aqueous liquid sufficiently uniformly. In addition, the above-mentioned continuous extrusion mixer preferably has such a structure that the water-absorbent resin powder is supplied and charged into an area where the first impellers are arranged, and that the aqueous liquid, preferably, the heated aqueous liquid, is supplied and charged into an area where the second impellers are arranged. Specifically, the water-absorbent resin is fed into the continuous extrusion mixer using the first impellers, and next, the aqueous liquid is supplied and charged into an area where the second impellers are arranged, thus stirring and mixing the water-absorbent resin powder and the aqueous liquid at a high speed in a moment. Therefore, the water-absorbent resin powder can be mixed with the aqueous liquid sufficiently uniformly without forming any "fisheye." Furthermore, as to the shape of the above-mentioned first impellers, the shape of a plate is preferable as the shape to generate an extrusion thrust, and as to the shape of the above-mentioned second impellers, the shape of a column is preferable as the shape to reduce the extrusion thrust to smaller than that by the first impellers and to thereby ensure sufficient mixing and stirring.

Incidentally, in the foregoing method (b) in which the granulation is carried out using a specific mixer, preferable other conditions (for example, the particle diameter of the granule, the temperature of the water-absorbent resin powder, the type and the amount of the aqueous liquid as used, and the mixing period of time) are the same as those in the foregoing method (a) in which the aqueous liquid is preheated prior to mixing and then the granulation is carried out. Specifically, the particle diameter is not larger than 20 mm, preferably, in the range of 0.3 to 10 mm, and more preferably, 0.3 to 5 mm. The heating temperature of the water-absorbent resin powder is, usually, not lower than 40° C., preferably, not lower than 50° C., but, usually, not higher than 100° C. In addition, the water content in the aqueous liquid is preferably not less than 90% by weight, more preferably, not less than 99% by weight, still more preferably, in the range of 99 to 100% by weight, and particularly preferably, 100% by weight. Furthermore, the amount of the aqueous liquid, as used, is, usually, not smaller than 1 part by weight, preferably, not smaller than 5 parts by weight, and, in view of granulation strength, particularly preferably in the range of 80 to 280 parts by weight, per 100 parts by weight of the water-absorbent resin powder. The mixing period of time is preferably not longer than 3 minutes, more preferably, not longer than 1 minute, and most preferably, in the range of 1 to 60 seconds.

The following water-absorbent resin granules in the present invention can be improved with regard to their granulation strength by drying them: a water-absorbent resin granule as obtained in the above way, particularly, a water-absorbent resin granule as obtained by mixing 100 parts by weight of the water-absorbent resin powder with 80 to 280 parts by weight of the aqueous liquid, and further a water-absorbent resin granule as obtained by either or both of (a) the foregoing method in which the aqueous liquid is preheated prior to mixing and then the granulation is carried out, and (b) the foregoing method in which the granulation is carried out using a specific mixer. If these water-absorbent resin granules are dried, the fine powder is united more strongly and thereby regenerated with as high a strength as a primary particle.

Incidentally, examples of the aqueous liquid, as used for the foregoing granulation in the present invention, include water and the below-mentioned hydrophilic organic solvents. Among them, particularly, heated water alone or heated water containing a small amount of crosslinking agents is preferable as the foregoing aqueous liquid, particularly, as the foregoing heated aqueous liquid. In this case, examples of usable crosslinking agents include surface-crosslinking agents with types and amounts as described hereinafter. The joint use of the crosslinking agent with the aqueous liquid in this way makes it possible to decrease the water-soluble content or further improve the granulation strength.

The method for drying is not specifically limited, and conventional dryers or ovens are widely used. The drying temperature is, preferably, relatively high, concretely, in the range of 110 to 300° C., more preferably, 120 to 200° C., still more preferably, 150 to 180° C., because the water-absorbent resin granule contracts when dried in these temperature ranges, resulting in formation of a strong, dry granule. The drying period of time is preferably not shorter than a certain period of time, for example, in the range of 5 minutes to 10 hours, in view of physical properties, and, after drying, the solid content is preferably not less than 90% by weight. Incidentally, the dry-treatment may be carried out either for only the water-absorbent resin granule, as produced in the present invention, or for a combination of the water-absorbent resin granule with the polymer gel which is obtained by the above-mentioned aqueous solution polymerization or reversed-phase suspension polymerization and has not yet been dried.

The water-absorbent resin granule-dried matter, which is obtained in the above way, is a strong granule as contracted by drying, but its particle size may be regulated by pulverizing, if necessary. After pulverizing, the average particle diameter of the water-absorbent resin granule-dried matter is in the range of, preferably, 150 to 800 µm, more preferably, 200 to 600 µm. In the present invention, it is preferred that a water-absorbent resin powder, of which at least 70% by weight has a particle diameter of not larger than 150 µm (but on average, for example, not larger than 100 µm), is granulated so as to have an average particle diameter of 150 to 600 µm.

It is preferable to subject the pulverization-classification product of the water-absorbent resin granule, as obtained in the above way, to the below-mentioned surface neighborhood crosslinking treatment. Specifically, it is preferable to carry out the following process steps: a water-absorbent resin granule is produced from a water-absorbent resin fine powder by the above-mentioned granulation process of the present invention, and then a water-absorbent resin with only a small content of the fine powder is produced by making a dry granule with an average particle diameter of 200 to 800 µm from the above-obtained water-absorbent resin granule, and then surface-crosslinked, thus obtaining a water-absorbent resin composition.

The following is a further explanation about the surface-crosslinking in the present invention.

In the present invention, the ratio by weight of the water-absorbent resin primary particle to the water-absorbent resin granule in the mixture of both is in the range of 98/2 to 2/98, preferably, 95/5 to 40/60. If a crosslinking agent is added to the mixture having the ratio by weight between the above materials within the above-mentioned range to thereby further crosslink the surface neighborhood of the mixture, then the water-absorbent resin composition with high granulation strength and high absorption capacity under a load, fitting the object of the present invention, can be obtained.

Too high a ratio of the water-absorbent resin granule involves granule particle fracture and too fast water absorption speed, and thus merely provides unsatisfactory results, or otherwise, too low a ratio of the water-absorbent resin granule renders the water absorption speed of the composition insufficient (incidentally, the particle mixture of the water-absorbent resin primary particle and the water-absorbent resin granule is hereinafter abbreviated as "water-absorbent resin particle mixture").

The surface-crosslinking agent, as used in the present invention, is not especially limited if it is a crosslinking agent with a functional group reactive upon a functional group that the water-absorbent resin has, and conventional ones in the art are favorably used. Examples thereof include: polyhydric alcohols such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-buten-1,4-diol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyamine compounds, such as ethylenediamine, diethylenetriamine, triethylenetetramine, tetraethylenepentamine, pentaethylenehexamine, and polyethylenimine, and their inorganic or organic salts (for example, azitidium salts); polyisocyanate compounds such as 2,4-tolylene diisocyanate and hexamethylene diisocyanate; polyoxazoline compounds such as 1,2-ethylenebisoxazoline; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolane-2-one, 1,3-dioxan-2-one, 4-methyl-1,3-dioxan-2-one, 4,6-dimethyl-1,3-dioxan-2-one, and 1,3-dioxopan-2-one; haloepoxy compounds, such as epichlorohydrin, epibromohydrin, and α-methylepichlorohydrin, and polyvalent amine addition products thereof (e.g. Kymene (trademark) made by Hercules); polyvalent metal compounds such as hydroxides or chlorides of zinc, calcium, magnesium, aluminum, iron, and zirconium. These surface-crosslinking agents may be used alone, or may be used in combinations of at least two thereof considering their reactivity. Among these surface-crosslinking agents, particularly preferred is at least one compound selected from the group consisting of polyhydric alcohol compounds, epoxy compounds, polyamine compounds and their salts, and alkylene carbonate compounds.

As is proposed in JP-A-06-184320 (U.S. Pat. No. 5,422,405), if a surface-crosslinking agent as used for the above-mentioned surface-crosslinking can react with a carboxyl group and comprises a combination of a first surface-crosslinking agent and a second surface-crosslinking agent whose solubility parameters are deferent from each other in the case where the water-absorbent resin particle mixture possesses a carboxyl group, then a water-absorbent resin composition with still more excellent absorption capacity under a load can be obtained. The above solubility parameter is a value as commonly used as a factor indicating the polarity of compounds. Values of solubility parameters, σ $(cal/cm^3)^{1/2}$, of solvents, as disclosed on pages 527–539 of *Polymer Handbook*, 3rd edition, published by WILEY INTERSCIENCE, are applied to the above-mentioned solubility parameter in the present invention. In addition, values, as applied to solubility parameters of solvents as not disclosed on the above-mentioned pages, are led by substituting Hoy's cohesive energy constant, as disclosed on page 525 of the *Polymer Handbook* above, for Small's equation as disclosed on page 524 of the *Polymer Handbook* above.

The above-mentioned first surface-crosslinking agent is preferably a compound which is reactive upon a carboxyl group and has a solubility parameter of 12.5 $(cal/cm^3)^{1/2}$ or more, further preferably, 13.0 $(cal/cm^3)^{1/2}$ or more.

The above-mentioned second surface-crosslinking agent is preferably a compound which is reactive upon a carboxyl group and has a solubility parameter less than 12.5 $(cal/cm^3)^{1/2}$, more preferably, in the range of 9.5 to 12.0 $(cal/cm^3)^{1/2}$.

The amount of the surface-crosslinking agent, as used, depends on the compounds as used as such, or on combinations thereof, but is preferably in the range of 0.001 to 10 parts by weight, more preferably, 0.01 to 5 parts by weight, per 100 parts by weight of the solid content of the water-absorbent resin particle mixture.

If the above-mentioned surface-crosslinking agents are used, the crosslinking density in the surface neighborhood of the water-absorbent resin particle mixture can be increased to a higher value than that inside. The amount of the surface-crosslinking agent, as used, larger than 10 parts by weight is unfavorable because it is not only uneconomical, but also is excessive to the formation of the optimal crosslinking structure in the water-absorbent resin composition. In addition, in the case where the amount of the surface-crosslinking agent as used is smaller than 0.001 parts by weight, effects for improving performances, such as the absorption capacity under a load, of the water-absorbent resin composition is unfavorably difficult to obtain.

When the water-absorbent resin particle mixture is mixed with the surface-crosslinking agent, in the present invention, water is preferably used as the solvent. The amount of water as used depends upon factors such as the type, particle diameter, or water content of the water-absorbent resin particle mixture, but is preferably in the range of 0 to 20 parts by weight (but not including 0 parts by weight), and preferably in the range of 0.5 to 10 parts by weight, relative to 100 parts by weight of the solid content in the water-absorbent resin particle mixture.

When the water-absorbent resin particle mixture is mixed with the surface-crosslinking agent, a hydrophilic organic solvent (aqueous liquid) may further be used, if necessary. Examples of the hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy(poly)ethylene glycol; amides such as ε-caprolactam and N,N-dimethylformamide; and sulfoxides such as dimethyl sulfoxide. The amount of the hydrophilic organic solvent as used depends upon factors such as the type, particle diameter, or water content of the water-absorbent resin particle mixture, but is preferably in the range of 20 parts by weight or less, more preferably, 0.1 to 10 parts by weight, relative to 100 parts by weight of the solid content in the water-absorbent resin particle mixture.

After the water-absorbent resin particle mixture is mixed with the surface-crosslinking agent, a heat-treatment is carried out to the resultant mixture, thus crosslinking the surface neighborhood of the water-absorbent resin particle mixture.

That is to say, the heat-treatment is preferable for activating the crosslinking agent in the surface neighborhood of the water-absorbent resin particle mixture if the reactivity of the crosslinking agent, the simplicity of production devices, and the productivity are considered. The temperature of the heat-treatment is fitly determined depending on factors such as the type of the surface-crosslinking agent as used or the objective crosslinking density, therefore, it is not especially limited, but it is preferably not lower than 80° C. When the temperature of the heat-treatment is lower than 80° C., not only the productivity deteriorates, but also no uniform crosslinking of the surface can be accomplished, because a long time is consumed for the heat-treatment, thus tending to result in the lowering of absorption properties under a load and in the remaining of the surface-crosslinking agent. The heating temperature is in the range of, preferably, 100 to 250° C., more preferably, 120 to 210° C. The heating period of time is preferably determined in the range of 1 minute to 3 hours.

The heat-treatment, as described above, can be carried out with conventional dryers or ovens. Examples of the dryers include channel type mixing dryers, rotary dryers, desk dryers, fluidized-bed dryers, gas-stream type dryers, and infrared dryers, but there is no especial limitation thereto.

In the present invention, it is permissible that the water-absorbent resin primary particle and the water-absorbent resin granule are separately surface-crosslinked before mixed. The foregoing surface-crosslinking method can, as is, be applied to the method for separately surface-crosslinking the water-absorbent resin primary particle and the water-absorbent resin granule.

The water-absorbent resin composition of the present invention as obtained in the above way is a novel water-absorbent resin composition comprising the mixture of the water-absorbent resin primary particle and the water-absorbent resin granule and displaying high physical properties, for example, an absorption capacity of at least 25 g/g for a physiological salt solution under a load of 50 $g/cm^2$.

Granules as obtained by conventional granulation processes can bear only a low load of at most about 20 $g/cm^2$ because of the granulation fracture, but the water-absorbent resin granule as obtained in the present invention displays excellent absorption even under a high load of 50 $g/cm^2$. Therefore, because of containing such a granule, the water-absorbent resin composition of the present invention displays a higher absorption capacity under a high load of 50 $g/cm^2$ than conventional ones, as well as excellent absorption speed, and further is free from the fine powder. In addition, the water-absorbent resin composition of the present invention preferably has the following properties: an absorption speed of 100 seconds or less; a water-soluble content of 15% by weight or lower, more preferably, 10% by weight or lower; a particle size distribution of 95% by weight or higher, more preferably, 98% by weight or higher, in terms of the proportion of particles with a particle size of 850 to 150 μm; and a granulation fracture ratio of 10% or less. Incidentally, the measurement methods for these physical properties are specified in the below-mentioned examples of some preferred embodiments according to the present invention.

It is permissible to afford various functions to the above-mentioned water-absorbent resin composition by further adding thereto materials such as disinfectants, antibacterial agents, perfumes, various inorganic powders, foaming agents, pigments, dyes, hydrophilic short fibers, fertilizers, oxidants, reductants, water, and salts. The water-absorbent resin composition of the present invention can be applied to uses of various conventional water-absorbent resins, but can favorably be used for absorbent articles such as absorbent-matter-containing sanitary materials, particularly, paper diapers, sanitary napkins, and incontinence pads, taking a serious view of the following performances as attained by the present invention: only a small amount of fine powder, a narrow particle size distribution, excellent absorption properties under a load, and excellent water absorption speed.

Hereinafter, an explanation is made about an embodiment of the present invention while referring to FIGS. 2 and 3.

Figure 2:
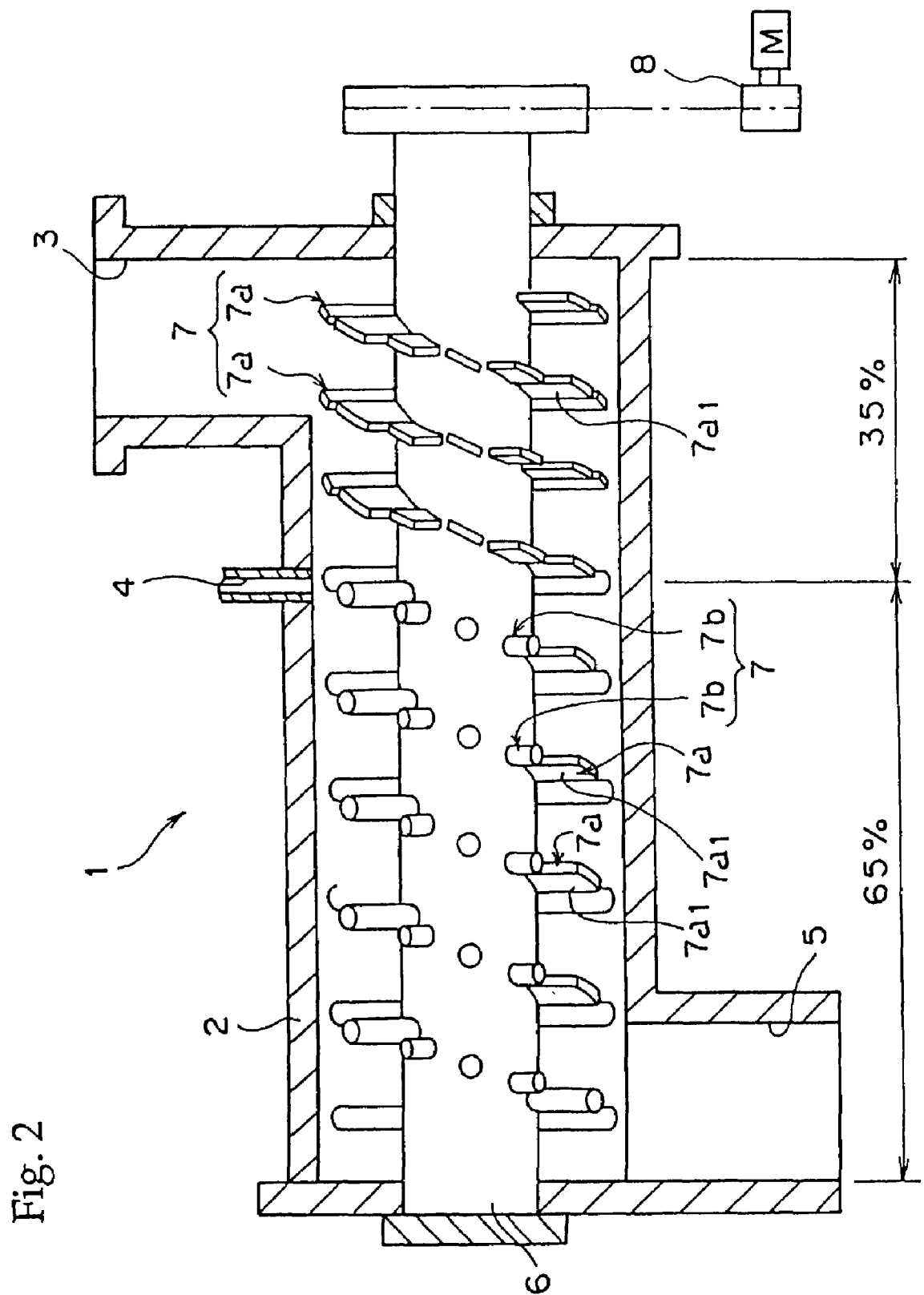
FIG. 2 is a section illustrating an embodiment of continuous extrusion mixers as included in production apparatuses as used in granulation method (b) for water-absorbent resins in the present invention.

As is illustrated in FIG. 2, a high-speed-stirring type continuous extrusion mixer 1, as used for the granulation method (b) and further, favorably, for adding and mixing a crosslinking agent into a mixture of a water-absorbent resin primary particle and a water-absorbent resin granule in accordance with the present invention, has, for example, a casing 2 as a horizontally fixed cylinder.

The casing 2 has: a material-supplying inlet 3, to project a powdery water-absorbent resin into, as illustrated in the right portion of the figure; a liquid-supplying inlet 4, to project an aqueous liquid for granulation into, on the discharge side of the material-supplying inlet 3; and a discharge outlet 5 on the left end side of the figure.

Incidentally, as is disclosed in JP-A-04-214734, the inner face of the casing 2 preferably comprises a base material, displaying an angle of 60° or more of contact with water and a thermal deformation temperature of 70° C. or higher, as an inner tube.

In other words, it should be noted that in the case where the base material displays an angle less than 60° of contact with water, the water-absorbent resin powder or the water-absorbent resin particle mixture might non-uniformly be mixed with the aqueous liquid or the crosslinking agent, and further that in the case where the thermal deformation temperature of the base material is lower than 70° C., the base material cannot sufficiently bear the heat as generated during the mixing. Therefore, when the base material does not satisfy the above conditions, it might be impossible to continue stable mixing.

Examples of the base material preferable for the inner face of the casing 2 include: synthetic resins such as polyethylene, polypropylene, polyester, polyamide, fluororesins, polyvinyl chloride, epoxy resins, and silicone resins; and the foregoing synthetic resins as reinforced by combining them with inorganic fillers, such as glass, graphite, bronze, and molybdenum disulfide, or with organic fillers such as polyimide.

In addition, among the above substances, particularly desired ones are fluororesins such as polyethylene tetrafluoride, polyethylene trifluoride, polyethylene trifluorochloride, ethylene tetrafluoride-ethylene copolymers, ethylene trifluorochloride-ethylene copolymers, propylene pentafluoride-ethylene tetrafluoride copolymers, perfluoroalkyl vinyl ether-ethylene tetrafluoride copolymers, and polyvinyl fluoride.

On the other hand, inside the casing 2, a rotary shaft 6 to rotationally drive with a driving motor 8 is furnished, and around the rotary shaft 6, a plurality of impellers 7 . . . are furnished.

The plurality of impellers 7 . . . are spirally arranged in sequence around the rotary shaft 6, and comprises a plurality of first impellers 7*a* . . . and a plurality of second impellers 7*b* . . . of which the shapes are different from those of the first impellers.

The first impellers 7*a* . . . are, for example, the shape of plates, such as rectangles, to generate an extrusion thrust. Incidentally, the first impellers 7*a* . . . are not necessarily limited to the shape of plates such as rectangles, but, as is illustrated by a continuous extrusion mixer 10 of FIG. 2, the shapes of paddle-like plates such as flippers and butterflies are also available along with the shapes of plates with not planar, but curved faces. In addition, as is illustrated in FIG. 2, the tip edges of the first impellers 7*a* . . . do not need to be linear, but, for example, may be arched, and further, the first impellers 7*a* . . . may, for example, have a blade edge like a chisel.

On the other hand, the second impellers 7*b* . . . are, for example, the shape of columns to generate an extrusion thrust smaller than that by the first impellers 7*a* . . . .

Incidentally, the second impellers 7*b* . . . are not limited to the shape of columns, either, but, for example, the shapes of bars or pins thinner than columns are also available. The shape of the tip thereof does not need to be planar, either, but may be spherical, for example, hemispherical.

As is illustrated in FIG. 2, the first impellers 7*a* . . . , which are plate-shaped, are furnished to a portion of the rotary shaft 6 with a length of about 35% from the end of the material-supplying inlet 3 wherein the entire length of the rotary shaft 6 present in the casing 2 is 100%, and, on the other hand, the second impellers 7*b* . . . , which are columnar, are furnished to a portion with a length of about 65% from the end on the side of the discharge outlet 5.

Thus, the first impellers 7*a* . . . give the water-absorbent resin and the aqueous liquid a sufficient extrusion thrust into the continuous extrusion mixer 1 or 10, and subsequently, the second impellers 7*b* . . . reduce the extrusion thrust to smaller than that by the first impellers 7*a* . . . , so that the mixing-stirring time can sufficiently be obtained to sufficiently carry out the mixing or reaction.

Figure 3:
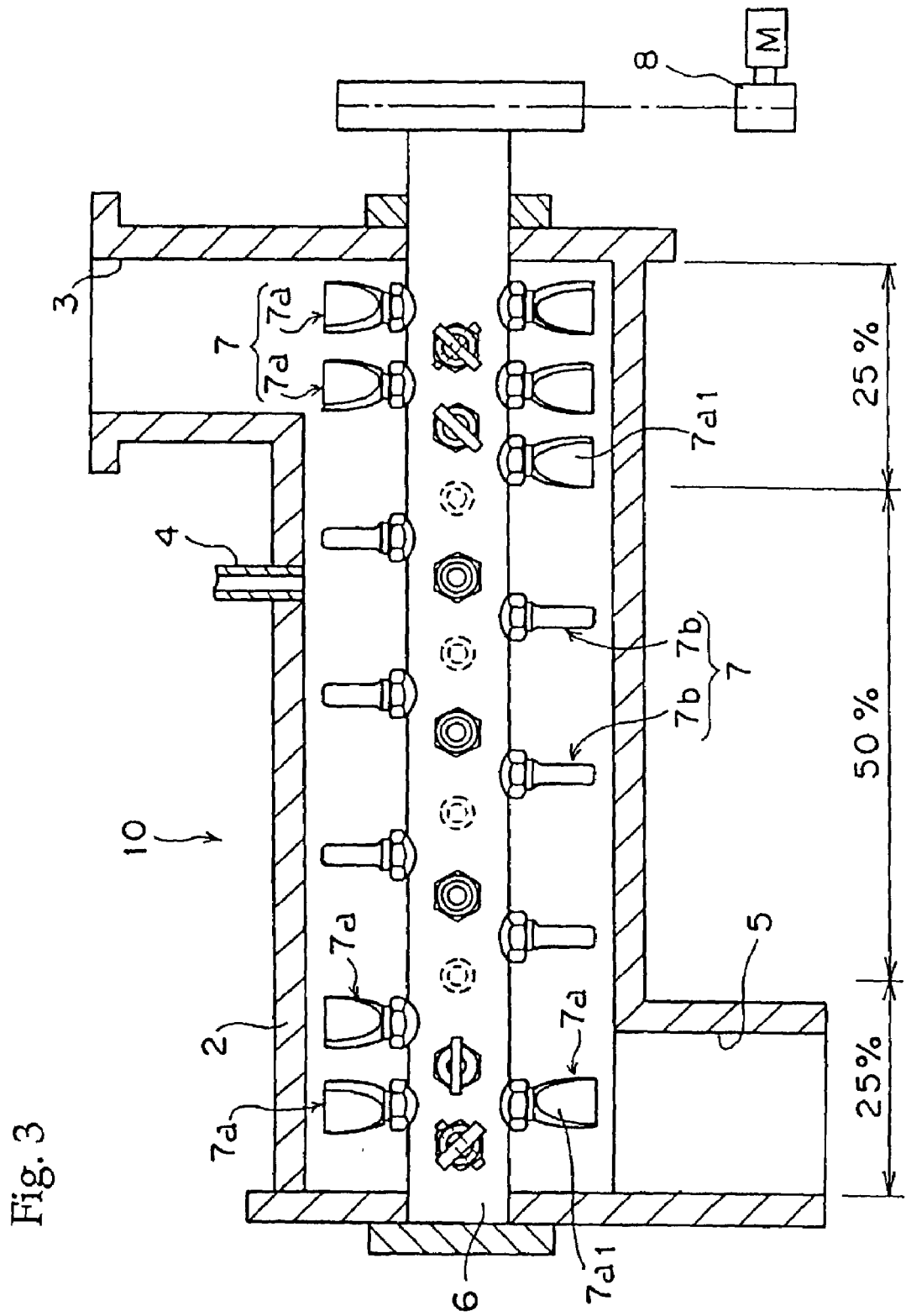
FIG. 3 is a section illustrating another embodiment of the above continuous extrusion mixers.

In addition, as is illustrated by the continuous extrusion mixer 10 of FIG. 3, some of the first impellers 7*a* . . . can be furnished on the further discharge side of the second impellers 7*b* . . . , if necessary. As to the continuous extrusion mixer 10, when the entire length of the rotary shaft 6 present in the casing 2 is 100%, the first impellers 7*a* . . . , which are paddle-shaped, are furnished both to a portion of the rotary shaft 6 with a length of about 25% from the end of the material-supplying inlet 3 and to a portion of the rotary shaft 6 with a length of about 25% from the end on the side of the discharge outlet 5, and further, the second impellers 7*b* . . . , of which the tips are hemispherically columnar, are furnished to the central portion other than the above.

The furnishing of the paddle-shaped first impellers 7*a* . . . on the discharge side, as mentioned above, enhances the extrusion thrust and favorably discharges the resultant mixing-reaction product.

Incidentally, the pitch, at which the impellers 7 . . . are arranged, is preferably set to match with an objective uniform mixing state.

In addition, in the continuous extrusion mixer 1 or 10, according to an embodiment of the present invention, the material-supplying inlet 3 to project a water-absorbent resin powder or the water-absorbent resin particle mixture into is made in an area where the first impellers 7a . . . are arranged, and the liquid-supplying inlet 4 to project an aqueous liquid or a crosslinking agent into is made in an area where the second impellers 7b . . . are arranged.

Specifically, when the water-absorbent resin and the aqueous liquid are mixed, both need to entirely contact each other as momentarily as possible. In the case where this is insufficient, so-called "fisheyes" are formed and the uniformity of the mixing is therefore damaged. Thus, in the present invention, because the water-absorbent resin is supplied with the first impellers 7a . . . into the continuous extrusion mixer 1 or 10, and because the high-speed stirring-mixing of the water-absorbent resin and the aqueous liquid is carried out with the second impellers 7b . . . in a moment, the water-absorbent resin and the aqueous liquid can sufficiently uniformly be mixed and reacted with each other.

In the case where a water-absorbent resin with a carboxyl group and an aqueous liquid containing materials reactable upon the carboxyl group, such as the crosslinking agent, are mixed or reacted with each other using the continuous extrusion mixer 1 having the above-mentioned constitution, the rotary shaft 6 is allowed to rotate, for example, at a high speed of about 500 to about 3,000 rpm, with the driving motor 8.

In this state, the water-absorbent resin is supplied from the material-supplying inlet 3, thus conveying the water-absorbent resin into the continuous extrusion mixer 1 by the extrusion thrust of the plate-shaped first impellers 7a . . . as spirally arranged.

Next, if the aqueous liquid is injected from the liquid-supplying inlet 4, the water-absorbent resin and the aqueous liquid containing materials such as the crosslinking agent are sufficiently mixed and reacted with each other due to the second impellers 7b . . . giving a small extrusion thrust, and uniformly mixed, and eventually the resultant mixing-reaction product is automatically discharged from the discharge outlet 5.

Next, this mixing-reaction product is, for example, dried or further surface-crosslinked with a heating device, thus forming a water-absorbent resin granule or composition with excellent strength properties.

Thus, the continuous extrusion mixers 1 and 10, according to embodiments of the present invention, have such a structure that the plurality of impellers 7 . . . are furnished around the rotary shaft 6 in the fixed casing 2 to mix and react the water-absorbent resin and the aqueous liquid together, and these impellers 7 . . . comprise at least two types of different shapes.

In conventional continuous extrusion mixers, a plurality of impellers of the same shape are arranged and, therefore, merely make a non-uniform stirring and an insufficient mixing.

As to the above-mentioned embodiments of the present invention, however, because the impellers 7 . . . comprise at least two types of different shapes, the mixing is carried out in at least two agitation states. As a result, the water-absorbent resin is efficiently mixed and reacted with the aqueous liquid, and uniform mixing can be ensured without any formation of "fisheyes." Thus, the water-absorbent resin granule and the water-absorbent resin composition, both of which make no restriction of the use method thereof in final products and constantly display excellent properties, can be provided.

In addition, because the plurality of impellers 7 . . . are spirally arranged in sequence, the extrusion thrust can sufficiently be ensured, and further, materials such as the water-absorbent resin can smoothly be extruded.

Furthermore, the plurality of first impellers 7a . . . and the plurality of second impellers 7b . . . are arranged in sequence around the rotary shaft 6 in the continuous extrusion mixers 1 and 10 according to embodiments of the present invention, wherein the first impellers 7a . . . are set on the material-supplying side and have shapes, such as plate shapes, to generate an extrusion thrust, and the second impellers 7b . . . are set on the discharge side of the first impellers 7a . . . and have shapes, such as columnar shapes, to generate an extrusion thrust smaller than that by the first impellers 7a . . . .

Thus, the first impellers 7a . . . give the water-absorbent resin and the aqueous liquid a sufficient extrusion thrust into the continuous extrusion mixers 1 and 10, and next, the second impellers 7b . . . reduce the extrusion thrust to smaller than that by the first impellers 7a . . . , so that the mixing-stirring time can sufficiently be obtained to sufficiently carry out the mixing or reaction. Therefore, the water-absorbent resin can be mixed or reacted with the aqueous liquid sufficiently uniformly.

In addition, because the first impellers 7a . . . are plate-shaped, the shape thereof is preferable as the shape to generate an extrusion thrust. Furthermore, because the first impellers 7b . . . are column-shaped, the shape thereof is preferable as the shape to reduce the extrusion thrust to smaller than that by the first impellers 7a . . . and to sufficiently ensure the mixing-stirring.

Furthermore, the inner face of the casing 2 in the continuous extrusion mixers 1 and 10 substantially comprises a base material displaying an angle of about 60° or more of contact with water and a thermal deformation temperature of about 70° C. or higher.

In other words, in the case where the base material displays an angle less than about 60° of contact with water, the water-absorbent resin might non-uniformly be mixed with the aqueous liquid, and further in the case where the thermal deformation temperature of the base material is lower than about 70° C., the base material cannot sufficiently bear the heat as generated during the mixing, and it might therefore be impossible to continue stable mixing. However, the embodiments of the present invention can avoid these problems.

Furthermore, as to the continuous extrusion mixer 10, because a plurality of first impellers 7a . . . are further furnished on the discharge side of the second impellers 7b . . . , the extrusion thrust during the discharge is sufficiently ensured, and therefore the discharge is favorably made.

In addition, the continuous extrusion mixers 1 and 10 have such a structure that the water-absorbent resin powder is supplied and charged into an area where the first impellers 7a . . . are arranged, and that the aqueous liquid is supplied and charged into an area where the second impellers 7b . . . are arranged.

Thus, the water-absorbent resin is supplied with the first impellers 7a . . . into the continuous extrusion mixer 1 or 10, and subsequently, the aqueous liquid is supplied and charged into an area where the second impellers 7b . . . are arranged, thus carrying out the high-speed stirring-mixing of the water-absorbent resin and the aqueous liquid with the second impellers 7b . . . in a moment. As a result, the water-absorbent resin and the aqueous liquid can sufficiently uniformly be mixed or reacted with each other.

Incidentally, the impellers 7 . . . in the above-mentioned embodiments of the present invention comprise the first impellers 7a . . . and the second impellers 7b . . . of the shape of two types, but the present invention is not limited to those embodiments. For example, impellers 7 . . . of further different shapes can further be furnished to enhance the stirring efficiency more greatly.

Hereinafter, the continuous granulation process of the present invention is explained in detail while referring to FIGS. 4 to 7.

In the continuous granulation process of the present invention, a water-absorbent resin powder and an aqueous liquid are supplied into a continuous extrusion mixer having a plurality of supplying-inlets along an arrangement of stirring-members, and then the water-absorbent resin powder and the aqueous liquid are mixed in the continuous extrusion mixer, thus continuously granulating the water-absorbent resin powder. In this process, when the water-absorbent resin powder and the aqueous liquid are supplied into the continuous extrusion mixer, the water-absorbent resin powder is supplied downstream of the aqueous liquid, so the amount of the materials as stuck into the continuous extrusion mixer can be decreased, and thus, stable granulation can continuously be carried out for a long term, and further a granule with excellent granulation strength can be obtained.

The water-absorbent resin powder and the aqueous liquid, as used in the continuous granulation process of the present invention, are both the same as mentioned previously.

In the aqueous liquid, water-insoluble inorganic or organic fine particulates may be dispersed. In addition, the aqueous liquid may contain an organic substance with a functional group reactive upon a functional group that the water-absorbent resin has. Examples of such an organic substance include a crosslinking agent. If the organic substance is used, the decrease of the water-soluble component and further improvement of the granulation strength can be accomplished.

In the continuous granulation process of the present invention, the ratio between the water-absorbent resin powder and the aqueous liquid, as used (supplied), may fitly be set depending upon factors such as combinations of the water-absorbent resin powder and the aqueous liquid, as used, and uses of the resultant granule, but the ratio is preferably set such that the amount of the supplied aqueous liquid is in the range of 30 to 400 parts by weight (more preferably, 80 to 280 parts by weight) per 100 parts by weight of the water-absorbent resin powder.

In the case where the amount of the aqueous liquid, as used, exceeds 400 parts by weight, there is no effect to improve the granulation strength rewarding the increase in the amount of the aqueous liquid as added, and there are disadvantages in view of the drying cost and so on. And, again, in the case where the amount of the aqueous liquid, as used, exceeds 400 parts by weight, physical properties might be deteriorated, or it might be impossible to mix the water-absorbent resin powder and the aqueous liquid enough uniformly.

On the other hand, in the case where the amount of the aqueous liquid, as used, is smaller than 30 parts by weight, the granulation strength might be insufficient, and the resultant final product might therefore not be able to display excellent properties, and further there is a possibility that any uniform granule could not be obtained due to non-uniform mixing.

In the continuous granulation process of the present invention, similarly to the foregoing method (a), the aqueous liquid may be preheated before mixed with the water-absorbent resin powder. The preheating temperature of the aqueous liquid may be the same as mentioned for the foregoing method (a).

If the aqueous liquid is preheated in the above way, then the particle diameter of the resultant granule can easily be controlled, and the resultant granule is prevented from being obtained as a united large gelatinous one, and the burden to a motor for working the continuous extrusion mixer can be lessened.

In addition, it is preferable that the water-absorbent resin powder is also preheated before mixing. The preheating temperature of the water-absorbent resin powder may also be the same as mentioned for the foregoing method (a).

The continuous granulation process of the present invention is particularly preferably applied to fine powders of water-absorbent resins (e.g. such powders having a particle diameter of not larger than 150 μm) among the water-absorbent resin powders.

The fine powder of the water-absorbent resin has the foregoing problems, and thus it is desired to reduce the fine powder content in the water-absorbent resin, whereas, as to the prior arts, continuous stable granulation of the fine powder of the water-absorbent resin was extremely difficult because of its large surface area, and further the fine powder of the water-absorbent resin had problems of physical property deterioration, granulation fracture, etc., so no effective process for granulating the fine powder has been established. However, the continuous granulation process of the present invention can be applied suitably for granulating such a fine powder of the water-absorbent resin.

Hereinafter, the continuous granulation process of the present invention is explained in more detail, especially, by exemplifying granulation of the water-absorbent resin powder as formed in the production process for the water-absorbent resin.

First, an explanation is hereinafter made on an example of the production process for the water-absorbent resin including the granulation process of the water-absorbent resin powder while referring to FIG. 7.

As to the water-absorbent resin powder to be granulated, its details such as specified examples, starting-materials (including monomers), and synthetic processes (polymerization processes) may be the same as mentioned previously.

Figure 7:
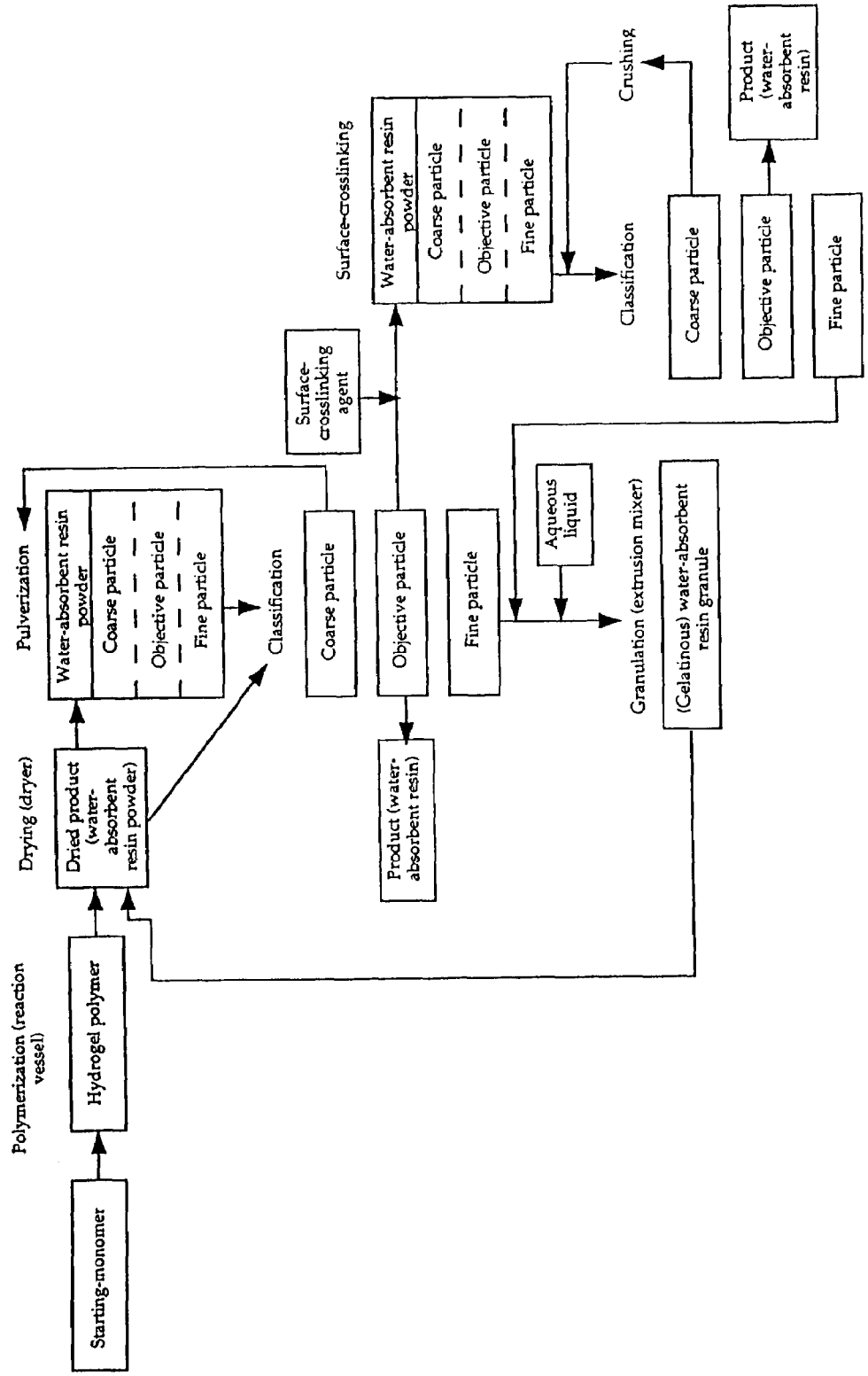
FIG. 7 is a flow chart of production process steps including the granulation of the water-absorbent resin powder.

As is illustrated in FIG. 7, when the water-absorbent resin is produced, the starting-monomers are first supplied into a reaction vessel, where a polymerization reaction is carried out.

In the case where the polymer as obtained by the above polymerization reaction is a hydrogel polymer, as is illustrated in FIG. 7, this hydrogel polymer is dried and, if necessary, pulverized, and then classified into a coarse particle, an objective particle, and a fine particle. Among them, the coarse particle is re-pulverized and re-classified. The objective particle is, as is or after surface-crosslinked, finished up to a product as a water-absorbent resin. The fine particle is granulated by mixing it with the aqueous liquid, and then dried and, if necessary, pulverized or surface-crosslinked, and thus finished up to a product. Thus, the fine particle can be recycled via the granulation process of the present invention, whereby the production efficiency of the water-absorbent resin can be enhanced. In addition, if the fine particle is surface-crosslinked after granulated, then a water-absorbent resin with still higher physical properties can be obtained.

Incidentally, the size of the objective particle is not especially limited, but fitly set depending upon uses of the objective particle. In embodiments of the continuous granulation process of the present invention, a water-absorbent resin powder with a particle diameter larger than a desired particle diameter of the objective particle is referred to as "coarse particle," and a water-absorbent resin powder with a particle diameter smaller than a desired particle diameter of the objective particle is referred to as "fine particle," but, when a water-absorbent resin powder with a particle diameter of not larger than 105 µm is included in the fine particle in a ratio of at least 50% by weight thereof, effects of the present invention are particularly greatly displayed.

In addition, the water-absorbent resin powder, as used in the continuous granulation process of the present invention, may be a surface-crosslinked one, or may be not. Thus, when the fine particle, as formed after surface-crosslinking the objective particle (mainly during the crushing), is granulated, the continuous granulation process of the present invention can also be applied. Incidentally, the coarse particle, as obtained in the above surface-crosslinking step, is crushed (pulverized) and classified again, thereby finally classified into the objective particle and the fine particle.

Furthermore, as is mentioned above, the fine particle may be either a classified one from the water-absorbent resin powder containing the fine particle in the production process for the water-absorbent resin, or an intentionally produced one by adjustment of pulverization or polymerization conditions for the purpose of enhancing the absorption speed. The water-absorbent resin powder, as granulated by the continuous granulation process of the present invention, may be any form of the following: only a fine particle of a water-absorbent resin (for example, a water-absorbent resin having a particle diameter of not larger than 150 µm); a mixture of the fine particle and larger particles therethan; a fine-particle-free water-absorbent resin (for example, consisting of particles having a particle diameter of 150 µm to 850 µm, but not including 150 µm). Among these water-absorbent resin powders, fine particles which have not yet been subjected to surface-crosslinking treatment are preferably used. In addition, the average particle diameter of the fine particle is preferably in the range of 150 to 10 µm, and the content of particles with a particle diameter of substantially not larger than 150 µm in the fine particle is preferably not lower than 70% by weight, and more preferably, not lower than 90% by weight. Furthermore, as is mentioned above, it is still more preferable that at least 50% by weight of the water-absorbent resin powder, as granulated by the continuous granulation process of the present invention, is a fine particle (fine powder) with a particle diameter of not larger than 105 µm. In addition, as to the shape of these fine particles, from the viewpoint of the granulation strength, an irregular shape as formed by aqueous solution polymerization is preferred to a spherical shape as formed by reversed-phase suspension polymerization.

Details of the surface-crosslinking agent and method, as used for the above-mentioned surface-crosslinking in the continuous granulation process of the present invention, may be the same as mentioned previously.

Hereinafter, the above process for continuously granulating a water-absorbent resin powder is explained in more detail.

In the continuous granulation process of the present invention, the continuous extrusion mixer, as used to granulate the water-absorbent resin powder, is not especially limited if it has a plurality of supplying-inlets to supply the water-absorbent resin powder and the aqueous liquid separately from each other, and further has a structure to continuously mix the water-absorbent resin powder and the aqueous liquid by stirring them while continuously discharging the resultant mixture.

Examples of such a continuous extrusion mixer include paddles mixer of Nishimura's model (made by Nishimura Kikai Seisakusho K. K.), Annular Layer Mixer (made by Draiswerke GmbH), Spiral Pin Mixer (made by Pacific Machinery & Engineering Co., Ltd.), continuous type Lödige Mixer (made by Gebrüder Lödige Maschinenbau GmbH), and Flow Jet Mixer (made by Funken Powtex). The continuous granulation process of the present invention can be carried out using these continuous extrusion mixers in such a manner that the water-absorbent resin powder is supplied downstream of the aqueous liquid, or using these continuous extrusion mixers as remodeled such that the water-absorbent resin powder can be supplied downstream of the aqueous liquid.

Figure 4:
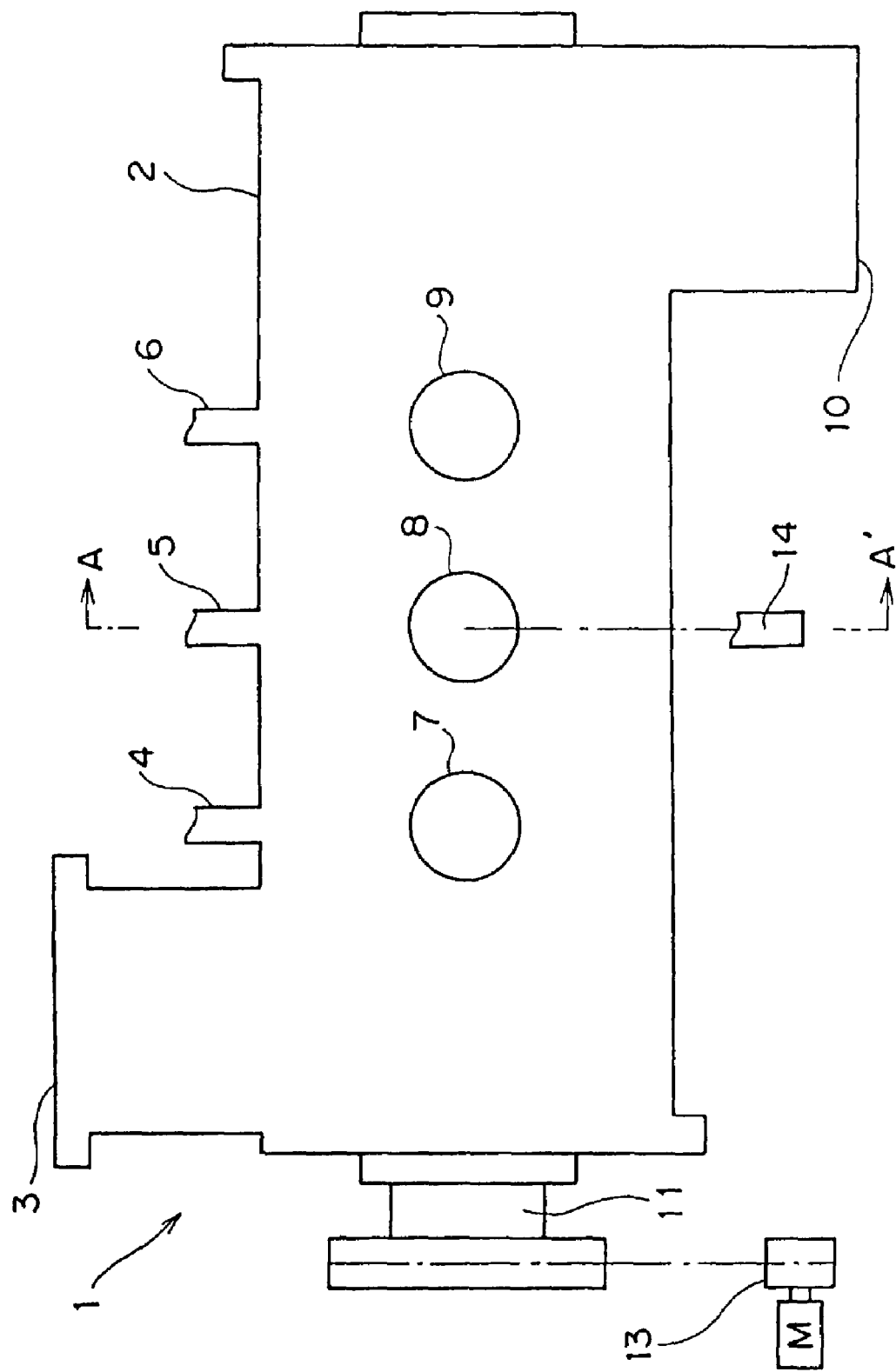
FIG. 4 is a schematic front view of a continuous extrusion mixer as used to continuously granulate a water-absorbent resin powder in accordance with an embodiment of the present invention continuous granulation process.
Figure 5:
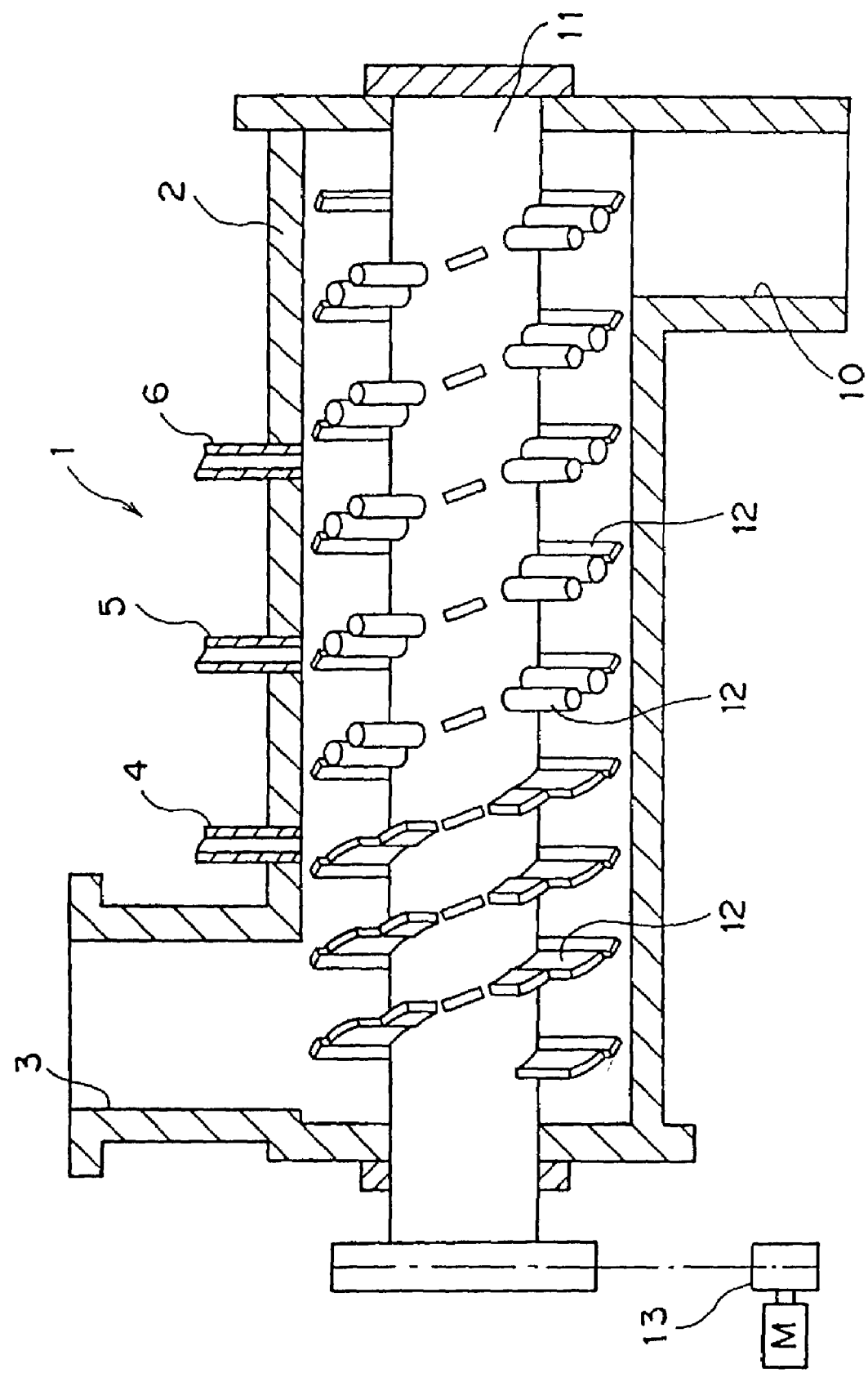
FIG. 5 is a structural view illustrating the continuous extrusion mixer of FIG. 4 with a portion thereof sectional.

As to the continuous extrusion mixer, a high-speed-stirring type continuous extrusion mixer 1 of FIGS. 4 and 5 is, for example, favorably used. This continuous extrusion mixer 1, for example, comprises: a casing 2 as a horizontally fixed cylinder; a rotary shaft 11 as furnished inside the casing 2 and rotationally driven with a driving motor 13; and a plurality of stirring-members (impellers) 12 . . . as furnished around the rotary shaft 11. Incidentally, the distance between the outer periphery of the rotary shaft 11 and the inner wall of the casing 2 is preferably set out of consideration for the stirring efficiency.

In the continuous extrusion mixer 1, the stirring-members 12 may, for example, be the shape of paddle-like plates such as flippers and butterflies, or the shape of plates such as rectangular, circular, oval, and triangular. In addition, the stirring-members 12 may be the shape of plates with not planar, but curved faces, and the tip edges of the stirring-members 12 may, for example, be arched. In addition, lower parts of the stirring-members 12 may, for example, be furnished with fixing-nuts. Furthermore, the stirring-members 12 may be prismatic, or, as is illustrated by FIG. 5, some of the stirring-members 12 . . . may be the shape not to generate an extrusion thrust, such as columnar or pin-like, if used in combinations with the plate-shaped or prismatic ones as mentioned above.

If the stirring-members 12 . . . are set in a state to mix the water-absorbent resin powder and the aqueous liquid while conveying (extruding) them, the shape or size thereof is not especially limited. In addition, the arrangement density or position of the stirring-members 12 . . . is not especially limited, but it is preferable that the stirring-members 12 . . . are arranged spirally around the rotary shaft 11 for the purpose of sufficiently ensuring the extrusion thrust and smoothly extruding the materials such as the water-absorbent resin powder.

Furthermore, it is preferable that the surfaces of the stirring-members 12 . . . and the rotary shaft 11 are coated with a film of materials such as Teflon resins, or plated, or coated with materials such as Teflon resin tubes, for the purpose of preventing adhesive materials, comprising a mixture of the water-absorbent resin powder and the aqueous liquid, from adhering to the stirring-members 12 . . . or the rotary shaft 11.

For the same reason, the inner face of the casing 2 is preferably provided with the same base material as used for the casing of the foregoing mixer of FIG. 2 or 3.

In addition, the casing 2 has a plurality of supplying-inlets 3 to 9 and a discharge outlet 10, and among them, the supplying-inlets 3, 4, 5, and 6 are arranged in this order from one end portion (left end portion in FIG. 4) toward the other end portion (right end portion in FIG. 4) of the casing 2 in a top wall of the horizontally fixed casing 2. In addition, the supplying-inlets 7, 8, and 9 are arranged in this order from one end portion (left end portion in FIG. 4) toward the other end portion (right end portion in FIG. 4) of the casing 2 in a side wall of the casing 2. Furthermore, the discharge outlet 10 is made at an end portion (right end portion in FIG. 4), opposite to the other end portion where the supplying-inlet 3 is made, in a bottom wall of the casing 2. In addition, the supplying-inlets 4 and 7 are set at the same distance from one end portion of the rotary shaft 11 in the casing 2. Similarly, the supplying-inlets 5 and 8 as well as the supplying-inlets 6 and 9 are set at the respective same distances from one end portion of the rotary shaft 11 in the casing 2. The supplying-inlets 3 to 9 have a structure free to be opened and closed, and those which are disused are closed, while those which are used are, for example, connected to a proportioning supply machine 14 such that the water-absorbent resin powder and the aqueous liquid can continuously be supplied at a certain rate.

In the continuous granulation process of the present invention, when the water-absorbent resin powder is granulated with the continuous extrusion mixer 1, the water-absorbent resin powder is supplied downstream of the aqueous liquid.

In conventional processes, when the water-absorbent resin powder and the aqueous liquid are mixed using an extrusion mixer, the water-absorbent resin powder is first projected from a powder-projecting inlet into the extrusion mixer, and the aqueous liquid is then injected from a liquid-injecting inlet as opened downstream of the powder-projecting inlet. However, such conventional processes have problems in that when the amount of the supplied aqueous liquid is increased to enhance the granulation strength, the water-absorbent resin powder and the aqueous liquid are only mixed non-uniformly, and in that adhesive materials, for example, comprising a mixture of the water-absorbent resin powder and the aqueous liquid, adhere to stirring-members, so the continuous granulation is difficult to carry out stably for a long term although it might be possible for a short term.

In comparison therewith, in the continuous granulation process of the present invention, because the water-absorbent resin powder is supplied downstream of the aqueous liquid, the adhesive materials are prevented from adhering to inner portions of the casing 2, especially, the stirring-members 12 . . . , inner portions of the water-absorbent resin powder-supplying inlets, or the neighborhood of the discharge outlet, whereby the granulation can be carried out continuously and stably for a long term. Furthermore, even when the amount of the supplied aqueous liquid is large, the water-absorbent resin powder and the aqueous liquid can uniformly be mixed, whereby a granule with excellent granulation strength can be obtained.

An operation to mix the water-absorbent resin powder and the aqueous liquid using the continuous extrusion mixer 1 of the above constitution is specified as follows: In this case, the rotary shaft 11 is first allowed to rotate, for example, at a high speed of about 500 to about 3,000 rpm, with the driving motor 13. Then, in this state, the aqueous liquid is supplied from the supplying-inlet 4 or 5 into the casing 2. The aqueous liquid, as supplied into the casing 2, is stirred with the stirring-members 12 . . . , for example, as spirally formed, while extruded toward the discharge outlet 10 by the extrusion thrust of the stirring-members 12, and then mixed with the water-absorbent resin powder as supplied from a supplying-inlet located downstream of the above supplying-inlet of the aqueous liquid, for example, from the supplying-inlet 8 or 9 corresponding respectively, and the resultant mixture (i.e. hydrogel granule) is continuously discharged from the discharge outlet 10.

In the continuous granulation process of the present invention, thus, the water-absorbent resin powder as, for example, supplied from the supplying-inlet 8 is mixed with the aqueous liquid as supplied from a supplying-inlet located upstream of the supplying-inlet 8, for example, from the supplying-inlet 4. In the continuous granulation process of the present invention, therefore, when the water-absorbent resin powder is added, the aqueous liquid is supplied upstream of the water-absorbent resin powder and then stirred with the stirring-members 12, as set between the supplying-inlets 4 and 8, thus forming a layer of the aqueous liquid in the casing 2.

Figure 6:
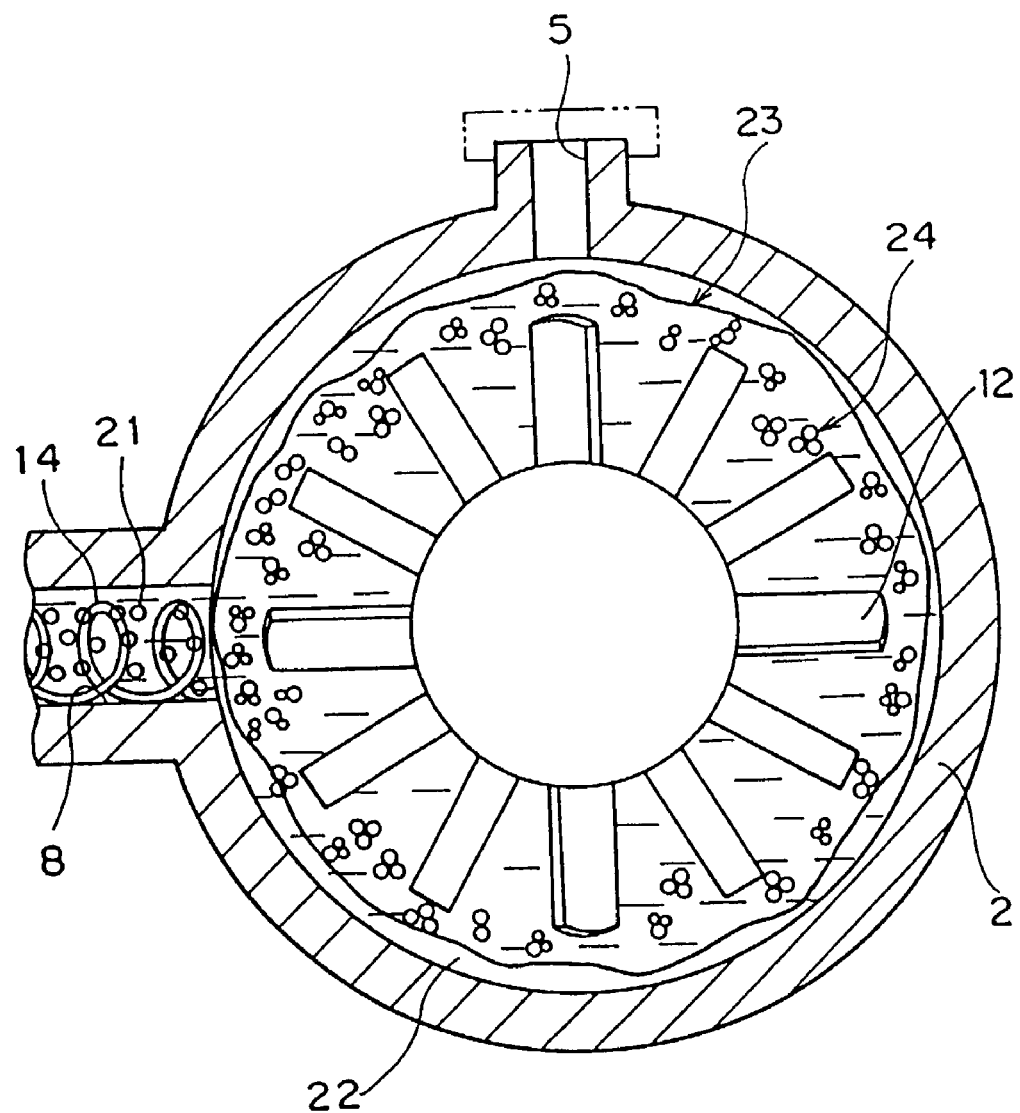
FIG. 6 is a section of the continuous extrusion mixer as cut along the A–A' arrow line in FIG. 4.

In the continuous granulation process of the present invention, therefore, as is illustrated in FIG. 6, a water-absorbent resin powder 21 as, for example, supplied from the supplying-inlet 8 comes into contact with a layer of a aqueous liquid 22. In the continuous granulation process of the present invention, therefore, the water-absorbent resin powder 21 and the aqueous liquid 22 come into contact with each other momentarily and uniformly as a whole, and immediately begin forming a granule (hydrogel granule 24). Accordingly, the continuous granulation process of the present invention makes it possible to efficiently mix the water-absorbent resin powder 21 and the aqueous liquid 22 without water absorption unevenness and thus can provide a granule with excellent granulation strength.

In addition, the continuous granulation process of the present invention has advantages in that: because the aqueous liquid 22 already exists where the water-absorbent resin powder 21 is supplied, there is no prior-art problem of that a large amount of the water-absorbent resin powder or the mixture thereof with the aqueous liquid sticks to the vicinity of the liquid injection inlet and to either or both of the inner wall of the mixer and the stirring-members as formed between the liquid injection inlet and the discharge outlet. Therefore, the hydrogel granule 24, as obtained by the continuous granulation process of the present invention, is extruded continuously and stably to the side of the discharge outlet 10 by the stirring-members 12 . . . . Incidentally, the water-absorbent resin powder 21, the aqueous liquid 22, and the hydrogel granule 24 in the casing 2 are subjected to the centrifugal force due to the rotation of the stirring-members 12 . . . , and most of these materials are rotated along an outer wall of the casing 2 and extruded to the side of the discharge outlet 10.

In the continuous granulation process of the present invention, the supply source of the water-absorbent resin powder 21 (proportioning supply machine 14) is not especially limited, but preferably has a proportioning ability and an extrusion ability to a certain degree. In the continuous granulation process of the present invention, because the aqueous liquid 22 already exists where the water-absorbent resin powder 21 is supplied, the supply source of the water-absorbent resin powder 21 is preferably such as has a proportioning supply ability that is not hindered by the aqueous liquid 22. Examples of the supply source satisfying such a demand include ACCU-RATE DRY MATERIAL FEEDERS (made by Accu-Rate Inc.) of the type that conveys materials by rotation of a single-shaft spiral member.

In addition, in the continuous granulation process of the present invention, when the water-absorbent resin powder 21 is granulated with the continuous extrusion mixer 1, the mixing of the aqueous liquid 22 and the water-absorbent resin powder 21 might be carried out while supplying a gas 23 upstream of the aqueous liquid 22. This is for the purpose of preventing a danger that the inside of the continuous extrusion mixer 1 might fall into a state of reduced pressure due to the rotation of the rotary shaft 11 of the continuous extrusion mixer 1, and that the water-absorbent resin powder 21, the aqueous liquid 22, or a mixture thereof might therefore flow backward from the discharge outlet 10 toward the supplying-inlets 3 to 9. Incidentally, in the continuous extrusion mixer 1, there is not only the above gas 23, but also, for example, a gas as generated due to vaporization of the aqueous liquid 22.

The above gas 23 is not especially limited if it is inert to the mixing of the aqueous liquid 22 and the water-absorbent resin powder 21, and preferable examples thereof include air and a nitrogen gas. The amount of the supplied gas 23 is set to prevent the water-absorbent resin powder 21, the aqueous liquid 22, or a mixture thereof from flowing backward from the discharge outlet 10 toward the supplying-inlets 3 to 9, namely, to maintain the internal pressure of the continuous extrusion mixer 1 within $-100$ to $100$ mmH$_2$O.

When the aqueous liquid 22 is, for example, supplied from the supplying-inlet 4, the gas 23 is supplied from the supplying-inlet 3 as located upstream of the supplying-inlet 4. The supplying-position of the gas 23 is not especially limited, but the clogging of the supplying-inlet of the gas 23 can be prevented by setting the supplying-position of the gas 23 upstream of that of the aqueous liquid 22.

When the entire length of the rotary shaft 11 present in the casing 2 is 100% and when the discharge outlet 10 is made at the right end of the casing 2, the aqueous liquid 22 is preferably supplied from a supplying-inlet which is made above a portion of the rotary shaft 11 with a length of about 0 to about 55% from the end portion (left end of the rotary shaft 11 inside the casing 2 in FIG. 4) opposite to the discharge outlet 10.

When the entire length of the rotary shaft 11 present in the casing 2 is 100% and when the discharge outlet 10 is made at the right end of the casing 2, the water-absorbent resin powder 21 is preferably supplied from a supplying-inlet which is made above a portion of the rotary shaft 11 with a length of about 10 to about 80% from the end portion (left end of the rotary shaft 11 inside the casing 2 in FIG. 4) opposite to the discharge outlet 10 (with the proviso that the water-absorbent resin powder 21 is supplied downstream of the aqueous liquid 22).

The supplying-position of the water-absorbent resin powder 21 is not especially limited if it is downstream of that of the aqueous liquid 22, but it is preferably 10 to 40% downstream of that of the aqueous liquid 22 when the entire length of the rotary shaft 11 present in the casing 2 is 100% and when the discharge outlet 10 is made at the right end of the casing 2. If the water-absorbent resin powder 21 is supplied 10 to 40% downstream of the aqueous liquid 22, then the aqueous liquid 22 can sufficiently be diffused into the casing 2 to form a layer thereof due to the stirring-members 12 . . . at the supplying-position of the water-absorbent resin powder 21, so the water-absorbent resin powder 21 and the aqueous liquid 22 can be brought into contact with each other with good efficiency and with no unevenness. And, in this case, depending upon the, revolution number of the rotary shaft 11 or upon the rotation speed of the end of the stirring-member 12, the distance of from the supplying-position of the water-absorbent resin powder 21 to the discharge outlet 10 is preferably at least 30%, more preferably, at least 50%, of the entire length of the rotary shaft 11 such that the residence time of the mixture of the water-absorbent resin powder 21 and the aqueous liquid 22 in the continuous extrusion mixer 1 can sufficiently be unsured.

Incidentally, depending upon the distance of from the supplying-position of the water-absorbent resin powder 21 to the discharge outlet 10, the aqueous liquid 22 might not sufficiently be absorbed into the water-absorbent resin powder 21, and the resultant hydrogel granule 24 therefore might contain fisheyes. However, if the continuous granulation process of the present invention is performed, then the contact between the water-absorbent resin powder 21 and the aqueous liquid 22 is carried out with no unevenness, so the stirring-members 12 . . . is not hindered from stirring (rotating) due to the adhesion thereto of a large amount of materials such as the water-absorbent resin powder 21 or a mixture thereof with the aqueous liquid 22. In addition, even if the resultant hydrogel granule 24 contains fisheyes immediately after discharged from the discharge outlet 10, it thereafter becomes uniform because the water-absorbent resin powder 21 absorbs the aqueous liquid 22 with time.

Examples of apparatuses, with which the present invention continuous granulation process in which the water-absorbent resin powder is supplied downstream of the aqueous liquid can be performed, other than the above continuous extrusion mixer include: Spiral Pin Mixer made by Pacific Machinery & Engineering Co., Ltd.; Flow Jet Mixer made by Funken Powtex; and Annular Layer Mixer made by Draiswerke GmbH.

The hydrogel granule 24, as obtained in the above way, preferably has an average particle diameter of 0.3 to 10 mm, more preferably, 0.5 to 8 mm, particularly preferably, 1 to 5 mm. In the case where the average particle diameter of the hydrogel granule 24 is smaller than 0.3 mm, the granulation ratio might be low, and further the granulation strength of a dry granule (water-absorbent resin granule), as obtained by drying the hydrogel granule 24, might be insufficient. In addition, in the case where the average particle diameter of the hydrogel granule 24 is larger than 10 mm, the physical properties might be deteriorated, or the fine powder content might be large.

That is to say, for the purpose of obtaining a water-absorbing agent having still more excellent granulation strength and excellent physical properties such as the absorption capacity under a load or the absorption speed, it is preferable to obtain a particulate hydrogel granule 24 with a moderate particle diameter and then shrink the resultant hydrogel granule 24 by drying.

As is aforementioned, thus, the hydrogel granule 24 as obtained in the above way is dried, classified, and then, as is or after surface-crosslinked, finished up to a product as a water-absorbent resin with excellent strength properties. If the hydrogel granule 24 is dried, its granulation strength can be enhanced, whereby the fine powder is united more strongly and thereby regenerated with as high a strength as a primary particle.

Incidentally, in the present invention, the hydrogel granule is such as has a water content of at least 10% by weight of the entire hydrogel granule. The hydrogel granule may be formed into a water-absorbent resin granule (dry granule) with a water content less than 10% by weight by drying.

The method for the above drying is not specifically limited, and conventional dryers or ovens are widely used. The drying temperature is, preferably, relatively high, concretely, in the range of 110 to 300° C., more preferably, 120 to 200° C., particularly preferably, 150 to 180° C. If the hydrogel granule 24 is dried, its shrinkage occurs, and as a result, a strong water-absorbent resin granule can be obtained.

The period of time to dry the hydrogel granule 24 is preferably not shorter than a certain period of time, more preferably, in the range of 5 minutes to 10 hours, in view of physical properties. In addition, after drying, the solid content is preferably not less than 90% by weight. Incidentally, the dry-treatment may be carried out either for only the hydrogel granule 24, as produced by the continuous granulation process of the present invention, or for a combination thereof with the hydrogel polymer which is obtained by the above-mentioned aqueous solution polymerization or reversed-phase suspension polymerization and has not yet been dried.

Incidentally, in the present invention, the water-absorbent resin granule is a particulate aggregate with a specific particle size as formed by aggregation of a plurality of water-absorbent resin powders 21 with the aqueous liquid 22. Incidentally, that the resultant mixture of the water-absorbent resin powder 21 and the aqueous liquid 22 is a granule (fine powder aggregate) can be judged from a fact that the aggregation of individual particles (of water-absorbent resin powder 21) can be confirmed with a optical micrograph of the hydrogel granule 24 or an electron micrograph as taken without pulverizing a dried product of the hydrogel granule 24, or from a fact that the particles swell as a plurality of discontinuous particles in a large excess of water or an aqueous liquid.

Incidentally, the above embodiment of the present invention has a constitution such that the discharge outlet 10 of the continuous extrusion mixer 1 is formed in the bottom wall of the casing 2, but the formation position of the discharge outlet 10 is not necessarily limited to in the bottom wall of the casing 2, but may, for example, be in an end face toward which the water-absorbent resin powder is conveyed in the casing 2.

Furthermore, the shape of the casing 2, namely, the shape of the continuous extrusion mixer, or the direction in which the casing 2 is fixed (set), is not especially limited, either, and may, for example, be the shape such that the casing 2 is fixed vertically (namely, in parallel with the gravity direction). In this case, the gravity is added to the extrusion thrust, whereby it might be possible to discharge the resultant hydrogel granule 24 more smoothly.

As is mentioned above, in the continuous granulation process of the present invention, when the water-absorbent resin powder and the aqueous liquid are supplied into the continuous extrusion mixer having a plurality of supplying-inlets along an arrangement of stirring-members and mixed therein, the water-absorbent resin powder is supplied downstream of the aqueous liquid, whereby the amount of the adhesive materials adhering to the continuous extrusion mixer can be reduced to carry out stable granulation continuously for a long term, and further a granule with excellent granulation strength can be obtained. Incidentally, in the case where the water-absorbent resin powder and the aqueous liquid are not sufficiently uniformly mixed, the aqueous liquid is not sufficiently absorbed into the central portion of the water-absorbent resin powder, and therefore the resultant granulation strength is insufficient, so the amount reverting to a ungranulated state increases due to drying and pulverizing steps. However, in the continuous granulation process of the present invention, a granule with as high a strength as a primary particle can be obtained.

(Effects and Advantages of the Invention):

The present invention displays the following excellent properties (1) to (7).

(1) Improvement of surface-crosslinking effects, prevention of reproduction of fine powder, and decrease of fine powder content: In the case where the granulation is carried out by conventional processes, such as a process comprising granulation after crosslinking the surface neighborhood of a water-absorbent resin and a process comprising the simultaneous steps of the granulation and the surface-crosslinking of the water-absorbent resin, the resultant granule is fractured due to mechanical stress during or after the granulation, resulting in the fracture of the surface crosslinkage and in the deterioration of the physical properties. In contrast therewith, in the present invention, a fine powder portion is first separated from the water-absorbent resin and then granulated, and the resultant granule is mixed with a primary particle of the water-absorbent resin residue as obtained by removing the fine powder from the water-absorbent resin in the above way, and the resultant mixture is treated with the surface-crosslinking agent. Therefore, the surface-crosslinking agent is uniformly distributed over the entire particles, so the water-absorbent resin composition with excellent physical properties can be obtained. In other words, because the granulation strength of the granule is high, the granulation fracture due to mechanical stress is difficult to occur, and as a result, the surface crosslinkage is difficult to fracture, and further the resultant water-absorbent resin composition reproduces the fine powder only a little and has only a low fine-powder content.

(2) Enhancement of physical strength of composition: Probably because the primary particle with high particle strength against mechanical stress supports the entire composition, the granulation fracture due to the mechanical stress of the water-absorbent resin granule in the composition is difficult to occur. Therefore, the resultant water-absorbent resin composition displays enhanced physical strength when compared with those which are obtained by surface-crosslinking either the primary particle containing the fine powder or the granule alone.

(3) Synergistic effects of physical properties: Conventional water-absorbent resins contain fine powders and therefore has a limitation in the improvement of physical properties. The removal of the fine powder is not only economically disadvantageous, but also reduces the surface area of the residue (water-absorbent resin primary particle) and therefore lowers the water absorption speed thereof. The production of only the water-absorbent resin granule comprises complicated process steps and involves a high cost of energy. However, if the water-absorbent resin primary particle and the water-absorbent resin granule, which is a granulation product of the fine powder, are obtained from the the water-absorbent resin and then mixed and then surface-crosslinked in accordance with the present invention, the water-absorbent resin composition with a high absorption capacity under a load as well as a fast absorption speed can be obtained.

(4) Enhancement of granulation strength: The enhancement in the granulation strength or in the absorption capacity under a load can further be designed using specific granulation processes.

(5) Excellent physical properties: Granules as obtained by conventional granulation processes can bear only a low load of at most about 20 $g/cm^2$ because of the granulation fracture, but the water-absorbent resin granule as obtained in the present invention displays excellent absorption even under a high load of 50 $g/cm^2$. Therefore, because of containing such a granule, the water-absorbent resin composition of the present invention displays a higher absorption capacity under a high load of 50 g/cm² than conventional ones, as well as excellent absorption speed, and further is free from the fine powder. In addition, the water-absorbent resin composition of the present invention preferably has the following properties: an absorption speed of 100 seconds or less; a water-soluble content of 15% by weight or lower, more preferably, 10% by weight or lower; a particle size distribution of 95% by weight or higher, more preferably, 98% by weight or higher, in terms of the proportion of particles with a particle size of 850 to 150 μm; and a granulation fracture ratio of 10% or less. Incidentally, the measurement methods for these physical properties are specified in the below-mentioned examples of some preferred embodiments according to the present invention.

(6) The continuous granulation process of the present invention makes effects to reduce the amount of the adhesive materials, adhering to the continuous extrusion mixer, to thereby carry out stable granulation continuously for a long term, and further to obtain a granule with excellent granulation strength.

(7) WO96/13542 discloses a process in which a water-absorbent resin powder gets, first, surface-crosslinked, and then classified, thus obtaining a primary particle (which has been surface-crosslinked) of a large particle diameter on a sieve, while granulating a fine particle (which has been surface-crosslinked) as passed through the sieve, and then the resultant granule (which has been surface-crosslinked) is mixed with the above primary particle which has been surface-crosslinked. As is mentioned above, in such a conventional process, a water-absorbent resin powder, first, gets surface-crosslinked. Because the surface-crosslinked water-absorbent resin powder has not yet been classified in this stage, however, it contains a particle of a very small particle diameter. Specifically describing, the surface-crosslinked water-absorbent resin powder in that stage contains not only a particle of a large particle diameter (i.e. particle obtained as a primary particle), but also a particle of a very small particle diameter (i.e. fine particle). Therefore, in the case where an aqueous liquid containing a surface-crosslinking agent is added to such a water-absorbent resin powder, the fine particle absorbs the aqueous liquid more than the primary particle, and therefore is strongly crosslinked. Thus, as to the particle of a large particle diameter, only its surface is crosslinked, whereas the fine particle is crosslinked up to its inside. The foregoing granule comprises such a fine particle as crosslinked up to its inside, and therefore is a particle inferior with regard to the water absorbency because of such an excessive crosslinking. In comparison therewith, as to the present invention, the granulation is beforehand carried out to enlarge the particle diameter, and then the surface-crosslinking is carried out, so the crosslinking of the granule can be prevented from advancing up to the inside of the granule.

DETAILED DESCRIPTION OF THE
PREFERRED EMBODIMENTS

Hereinafter, the present invention is more specifically illustrated by the following examples of some preferred embodiments in comparison with comparative examples not according to the invention. However, the invention is not limited to the below-mentioned examples.

The physical properties of water-absorbent resins were measured as follows:

(Water Absorption Capacity)

A nonwoven fabric bag (60 mm×60 mm), in which about 0.2 g of a water-absorbent resin powder or composition was put uniformly, was immersed into a 0.9 wt % aqueous sodium chloride solution (physiological salt solution). After 60 minutes, the bag was drawn up and then drained at 250 G with a centrifuge for 3 minutes. Then, weight $W_1$ (g) of the bag was measured. In addition, the same procedure as the above was carried out using no water-absorbent resin, and weight $W_0$ (g) of the resultant bag was measured.

Thus, the water absorption capacity (g/g) was calculated from these weights $W_1$ and $W_0$ in accordance with the following equation:

$$\text{water absorption capacity (g/g)} = (\text{weight } W_1 \text{ (g)} - \text{weight } W_0 \text{ (g)})/0.2 \text{ (g)}.$$

(Water-soluble Content)

First, 0.50 g of a water-absorbent resin powder or composition was dispersed into 1,000 ml of deionized water, and stirred for 16 hours, and then filtered with a filter paper (TOYO, No.6). The solid content in the resultant filtrate was measured to calculate the water-soluble content in accordance with the following equation:

$$\text{water-soluble component (wt \%)} = (\text{liquid weight (g)}) \times (\text{solid content in filtrate (wt \%)})/0.5 \text{ (g)}.$$

(Absorption Capacity Under Load)

Hereinafter, a measurement apparatus as used for measuring the absorption capacity under a load is explained while referring to FIG. 1.

As is shown in FIG. 1, the measurement apparatus comprises: a scale 21; a vessel 22 of a predetermined capacity as mounted on the scale 21; an air-inhaling pipe 23; an introducing tube 24; a glass filter 26; and a measurement part 25 as mounted on the glass filter 26.

The vessel 22 has an opening part 22a on the top and an opening part 22b on the side. The air-inhaling pipe 23 is inserted in the opening part 22a of the vessel 22, and the introducing tube 24 is fitted to the opening part 22b.

In addition, the vessel 22 contains a predetermined amount of physiological salt solution 32. The lower part of the air-inhaling pipe 23 is submerged in the physiological salt solution 32. The air-inhaling pipe 23 is fitted to keep the internal pressure of the vessel 22 almost atmospheric. The glass filter 26 is formed in a diameter of 55 mm. The vessel 22 and the glass filter 26 are connected to each other through the introducing tube 24 made of a silicone resin. In addition, the position and the level of the glass filter 26 are fixed relative to the vessel 22.

The measurement part 25 comprises: a filter paper 27; a supporting cylinder 28; a wire net 29 as attached to the bottom of the supporting cylinder 28; and a weight 30; and the measurement part 25 is formed by mounting the filter paper 27 and the supporting cylinder 28, as bottomed with a wire net 29, in this order on the glass filter 26 and further mounting the weight 30 inside the supporting cylinder 28, namely, on the wire net 29. The wire net 29 is made of stainless steel and formed in 400 mesh (mesh size: 38 μm). In addition, the upper face, namely, the contact face between the wire net 29 and a water-absorbent resin composition 31, of the wire net 29 is set to be as high as a lower part 23a of the air-inhaling pipe 23. An arrangement is made such that a predetermined amount of water-absorbent resin composition with a predetermined particle diameter can uniformly be spread on the wire net 29. The weight 30 is adjusted in weight such that a load of 50 g/cm$^2$ can uniformly be applied to the water-absorbent resin composition 31 on the wire net 29.

The absorption capacity under a load was measured with the measurement apparatus having the above-mentioned constitution. The measurement method is hereinafter explained.

First, predetermined preparatory operations are made, in which, for example, a predetermined amount of the physiological salt solution 32 is placed into the vessel 22, and the air-inhaling pipe 23 is inserted into the vessel 22. Next, the filter paper 27 is mounted on the glass filter 26, and further, in parallel with this mounting operation, 0.9 g of water-absorbent resin composition is uniformly spread inside the supporting cylinder 28, namely, on the wire net 29, and the weight 30 is then put on the water-absorbent resin composition 31.

Next, the wire net 29 of the supporting cylinder 28, on which the water-absorbent resin composition 31 and the weight 30 are put, is mounted on the filter paper 27 concentrically with the glass filter 26.

Then, the weight of the physiological salt solution 32, as absorbed by the water-absorbent resin composition 31 over a period of 60 minutes since the supporting cylinder 28 is mounted on the filter paper 27, is determined from a measured value with the scale 21. The same procedure as the above was carried out without using the water-absorbent resin composition 31, and the weight of the physiological salt solution 32, as absorbed by materials other than the water-absorbent resin composition 31, such as the filter paper 27, was determined from a measured value with the scale 21 and regarded as a blank value. Subsequently, the correction by subtracting the blank value was carried out, and the net weight of the physiological salt solution 32, as absorbed by the water-absorbent resin composition 31, was divided by the weight of the water-absorbent resin composition 31 (0.9 g), thus calculating an absorption capacity (g/g) under a load of 50 g/cm$^2$.

(Water Absorption Speed)

First, various reagents were dissolved into water, thus preparing an aqueous solution containing sodium cation of 600 to 700 ppm, calcium cation of 65 to 75 ppm, magnesium cation of 55 to 65 ppm, potassium cation of 1,100 to 1,200 ppm, phosphorus of 240 to 280 ppm, sulfur of 450 to 500 ppm, chlorine of 1,100 to 1,300 ppm, and sulfuric acid ion of 1,300 to 1,400 ppm. This aqueous solution was used as an artificial urine.

Next, 0.358 g of a water-absorbent resin composition, as classified into 300 to 850 μm with a JIS standard sieve, was placed into a glass-made test tube (inner diameter=about 14.1 mm, height=about 126 mm), and 10.00 g of the above artificial urine was then poured into the test tube at once. The number of the seconds in time, which had passed until the entirety of the 10.00 g of the artificial urine had been absorbed by the 0.358 g of the water-absorbent resin composition and had formed a swollen gel of 28 times the original, was measured and regarded as the absorption speed.

(Granulation Strength)

The granulation strength was measured by a method as disclosed in JP-A-09-235378. Hereinafter, the way to apply the impact force (B), as disclosed therein, is specifically explained.

A vessel, as used when applying the impact force (B) to the above water-absorbent resin granule, has an inner cap and an outer cap on a transparent glass-made vessel body with a height of about 10.8 cm, a diameter of about 6.2 cm, and a capacity of 225 g. As to such a vessel, for example, a so-called mayonnaise bottle (trade name: A-29), made by Yamamura Glass K. K., is favorably used. In addition, preferable examples of the above glass beads are those which are made of soda-lime glass and used as fractional distillation fillers with an average bead diameter of about 6 mm as made uniform within the bead diameter range of about 5.9 to about 6.4 mm. Incidentally, 10.0 g of the above glass beads correspond to 31 to 33 in number of the glass beads.

When the impact force (B) is applied to a water-absorbent resin composition, 30.0 g thereof is placed into the vessel body of the above vessel along with 10.0 g of the above glass beads, and then the inner and outer caps are both closed. Then, this vessel is fixed to a dispersing machine (No. 488 dispersing machine for test, made by Toyo Seiki Seisakusho K. K.) by interposing the vessel between an upper and a lower clamp as equipped to the dispersing machine, and a vibration of a vibration speed revolution number of 750 c.p.m. is given to the vessel using an alternating electric power source of 100 V/60 Hz for 30 minutes. As a result, the vessel, as fixed to the dispersing machine, pivots at angles of 12.5° left and right each (25° in total) to a face to which the upper and the lower clamp are fitted, and simultaneously therewith, the vessel vibrates 8 mm back and forth each (16 mm in total), thus applying the impact force to the water-absorbent resin composition in the vessel.

The fracture ratio of the water-absorbent resin composition (hereinafter referred to as "granulation fracture ratio") is a percentage value as determined by measuring the weight of a portion, as fractured due to the above application of the impact force (B) for 30 minutes and the above vibration along with the glass beads, of the water-absorbent resin composition in the vessel and by dividing the above-measured weight of the fractured portion of the vibrated water-absorbent resin composition by the original weight of the water-absorbent resin composition as charged.

Thus, the above granulation fracture ratio can be determined by measuring, by ROTAP Sieve Tester with JIS standard sieves, the weight of a particle with a certain particle size (e.g., what passed through meshes of 150 μm) resultant from the fracture by applying the impact force (B).

PRODUCTION EXAMPLE 1-1 FOR WATER-ABSORBENT RESIN POWDER

An aqueous solution was prepared by dissolving polyethylene glycol diacrylate of 0.05 mol % as an internal crosslinking agent into 5,500 g of an aqueous solution of sodium acrylate with a neutralization ratio of 75 mol % (monomer concentration: 33 wt %), and then degassed with a nitrogen gas for 30 minutes, and then supplied into a reaction vessel as prepared by capping a stainless-steel-made double-arm type kneader of a capacity of 10 liters having two sigma type wings and a jacket. While maintaining the reaction system at 20° C., the replacement with a nitrogen gas in the reaction system was continued. Next, while rotating the wings, 2.9 g of sodium persulfate and 0.16 g of L-ascorbic acid were added in the form of 10 wt % aqueous solutions of them each. As a result, 1 minute after, a polymerization reaction got started and, 16 minutes after, the reaction system reached the peak temperature of 83° C., when the resultant hydrogel polymer was a finely particulated one with a size of about 5 mm. Then, the stirring was further continued, and the resultant hydrogel polymer was separated out 60 minutes after the initiation of the polymerization.

The resultant finely-particulated hydrogel polymer was spread on a wire net with a mesh size of 300 µm (50 mesh) and then dried at 150° C. with hot air for 90 minutes. Then, the resultant dried product was pulverized with a roller mill, and then classified with a mesh of 850 µm, thus obtaining a pulverized water-absorbent resin powder (A) with an average particle diameter of 300 µm, a particle diameter distribution where the proportion of the resin with a particle diameter smaller than 150 µm was 15% by weight, and a water content of 6% by weight.

Then, the water-absorbent resin powder (A) was classified with a sieve of the mesh size of 150 µm into a water-absorbent resin powder ($A_1$) of 850 to 150 µm and a water-absorbent resin powder ($A_2$) smaller than 150 µm. Incidentally, the powders ($A_1$) and ($A_2$) are a primary particle and a fine powder, respectively, as referred to in the present invention. The water-absorbent resin powder (A) showed a water absorption capacity of 42 g/g and a water-soluble content of 10% by weight.

PRODUCTION EXAMPLE 1-2 FOR
WATER-ABSORBENT RESIN POWDER

A reaction solution was prepared by dissolving trimethylolpropane triacrylate of 0.04 mol % as an internal crosslinking agent into 5,500 g of a 38 wt % aqueous solution of sodium acrylate (neutralization ratio: 75 mol %) as a monomer component in the same polymerization vessel as used in Production Example 1-1. Next, 2.9 g of ammonium persulfate and 0.02 g of L-ascorbic acid were added to the above reaction solution to carry out a polymerization reaction in the same way as of Production Example 1-1. The resultant hydrogel polymer was dried in the same way as of Production Example 1-1 and then pulverized with a roll granulator type pulverizer as equipped with three pulverizing rolls which were stepwise arranged at predetermined intervals (roll gaps: about 1.63 mm, about 0.43 mm, and about 0.15 mm). Then, the resultant pulverization product was classified with a JIS standard sieve of a mesh size of 850 µm, thus obtaining a pulverized water-absorbent resin powder (B) with an average particle diameter of 300 µm. This water-absorbent resin powder (B) showed a water absorption capacity of 33 g/g and a water-soluble content of 10 wt %.

The water-absorbent resin powder (B) was further classified with a JIS standard sieve of a mesh size of 150 µm, thus obtaining a water-absorbent resin powder ($B_1$) of 86.3 wt % with a particle diameter of 850 to 150 µm and a water-absorbent resin powder ($B_2$) of 13.7 wt % with a particle diameter smaller than 150 µm.

GRANULATION EXAMPLES AND
COMPOSITIONS USING THEM

Granulation Example 1

Granulation with Preheated Aqueous Liquid

First, 200 g of the water-absorbent resin powder ($A_2$) with a particle diameter smaller than 150 µm, as obtained in Production Example 1-1 above, was placed into a mortar mixer of 5 liters (the temperature of a vessel of 5 liters in the mixer was kept with a bath of 70° C.) as produced by Nishi Nihon Shikenki Seisakusho K. K. Then, 300 g of water, as heated to 90° C., was added at once while rotating the impeller of the above mortar mixer at a high speed using an alternating electric power source of 60 Hz/100 V.

The water-absorbent resin powder ($A_2$) was mixed with water within 10 seconds, and the resultant entire contents of the mixer was a gelatinous water-absorbent resin granule with a particle diameter of about 3 to about 10 mm. In the mortar mixer, the water-absorbent resin granule was in pieces, and there was no sign that the granule was kneaded by mixing with the impeller.

After the high-speed stirring in the mortar mixer for 3 minutes, the resultant water-absorbent resin granule in pieces was separated from the mixer, and then placed on a wire net of the mesh size of 300 µm, and then dried in a hot-air circulation type dryer at 150° C. for 2 hours. Next, the resultant dry granule was pulverized with a roller mill under the same conditions as those in Production Example 1-1, and then classified into particles with a particle diameter of 850 to 150 µm, thus obtaining a water-absorbent resin granule (1) with a water absorption capacity of 42 g/g and a water-soluble content of 10% by weight. The ratio of the water-absorbent resin granule with a particle diameter of 850 to 150 µm was 83% of the roller mill pulverization product. Incidentally, a few particles of the water-absorbent resin granule (1) were extracted, and the physiological salt solution was then added dropwise to each particle, and the liquid-absorption behavior was then observed. As a result, the collapse to small fine particles was seen with the progress of swelling.

Granulation Example 2

Granulation with Unheated Water

The same procedure as of Granulation Example 1 was carried out except that the water to be added to 200 g of the water-absorbent resin powder ($A_2$) was gradually added with a spray, in other words, except that it took 30 minutes to add 300 g of water.

As water was added, the water-absorbent resin powder ($A_2$) grew aggregated to form a huge mass with a size of 20 to 50 mm, and finally, entirely became lumped and got kneaded. The resultant lumpy hydrogel aggregate was separated from the mixer, and then sliced into the size of not larger than 10 mm with a cutter, and then placed on a wire net of the mesh size of 300 µm, and then dried in a hot-air circulation type dryer at 150° C. for 2 hours.

Then, the resultant dry product was pulverized with a roller mill, and then classified into particles with a particle diameter of 850 to 150 µm, thus obtaining a water-absorbent resin granule (2) with a water absorption capacity of 42 g/g and a water-soluble content of 14% by weight. A few particles of the water-absorbent resin granule (2) were extracted, and the physiological salt solution was added dropwise to each particle, and the absorption behavior was observed. The particles swelled slowly without collapse.

Comparative Example 1-1

Surface-crosslinking of Granule Alone

An aqueous liquid of surface-crosslinking agents, comprising 0.05 parts by weight of ethylene glycol diglycidyl ether, 1.0 part by weight of propylene glycol, 3 parts by weight of water, and 0.9 parts by weight of isopropanol, was mixed with 100 parts by weight of the water-absorbent resin granule (1) as obtained in Granulation Example 1. The resultant mixture was heated at 195° C. for 30 minutes, thus obtaining a comparative water-absorbent resin composition (1) with a water absorption capacity of 33 g/g and an absorption capacity of 27 g/g under a load. However, when this swollen gel was strongly pushed with a finger, the granulation was fractured, and a fine gel with poor liquid-permeability was formed.

Comparative Example 1-2

Surface-crosslinking of Primary Particle Alone

The same surface-crosslinking as of Comparative Example 1-1 was carried out to 100 parts by weight of the water-absorbent resin powder ($A_1$) which was a primary particle as obtained in Production Example 1-1. As a result, a comparative water-absorbent resin composition (2) with a water absorption capacity of 33 g/g and an absorption capacity of 27 g/g under a load was obtained.

Comparative Example 1-3

Surface-crosslinking of Mixture of Primary Particle and Fine Powder

The same procedure as of Comparative Example 1-1 was carried out to the water-absorbent resin powder (A) with a particle diameter smaller than 850 μm as obtained in Production Example 1-1 above. As a result, a comparative water-absorbent resin composition (3) with a water absorption capacity of 33 g/g and an absorption capacity of 24 g/g under a load was obtained.

Example 1-1

Surface-crosslinking of Particle Mixture

The same procedure as of Comparative Example 1-1 was carried out to 100 parts by weight of a particle mixture comprising 15 parts by weight of the water-absorbent resin granule (1) as obtained in Granulation Example 1 and 85 parts by weight of the water-absorbent resin powder ($A_1$) which was a primary particle as obtained in Production Example 1-1. As a result, a water-absorbent resin composition (1) was obtained.

Granulation Example 3

Granulation with Specific Mixer

The water-absorbent resin fine powder ($B_2$), as obtained in Production Example 1-2 above, and ion-exchanged water were continuously mixed by projecting the water-absorbent resin fine powder ($B_2$) into the continuous extrusion mixer 1 of FIG. 2 at a rate of 2 kg/minute and, in parallel therewith, projecting the ion-exchanged water from the liquid-supplying inlet 4 with a diameter of 5 mm of the above continuous extrusion mixer 1 in a ratio of 130 parts by weight per 100 parts by weight of the water-absorbent resin fine powder ($B_2$). As a result, a particulate uniform gelatinous water-absorbent resin granule was continuously discharged from the discharge outlet. The resultant particulate gelatinous granule was an aggregate of each particle, and most thereof was a uniform gelatinous granule with a particle diameter of about 1 mm to about 5 mm. In addition, the above gelatinous granule had a solid content of 43.6% by weight. Incidentally, the solid content of the gelatinous granule is the amount (content) of the water-absorbent resin in the gelatinous granule.

The above gelatinous granule was spread into a thickness of about 5 cm on a JIS standard wire net of the mesh size of 300 μm and then dried with a hot-air circulation type dryer of 160° C. As a result, the above gelatinous granule was dried uniformly and sufficiently so as to have a solid content of at least 90 wt %, thus obtaining a powdery dry granule of which the particles could easily be pulverized even by hand. The proportion of lumps larger than 10 mm in the dry granule was only 5%.

Next, this dry granule was pulverized with the foregoing roller mill (however, the roll gaps were widened and finally evened to about 0.27 mm) and then classified with a JIS standard sieve of a mesh size of 850 μm, thus obtaining a water-absorbent resin granule (3).

The particle size distribution was measured for the water-absorbent resin granule (3), the water-absorbent resin powder (B), the water-absorbent resin powder ($B_1$), and the water-absorbent resin fine powder ($B_2$), as obtained in the above ways, and results thereof are shown in Table 2. In addition, in spite of the use of the water-absorbent resin fine powder ($B_2$), the water-absorbent resin granule (3) was a granule (aggregate) of particles, of which about 80% had a particle diameter of 300 to 850 μm, and as a result, the water-absorbent resin granule (3) was a granule (aggregate) which had such a high granulation strength that the granulation fracture ratio, as defined by the impact force (B), was 2.4 wt %.

Granulation Example 4

Granulation with Preheated Aqueous Liquid in Specific Mixer

The same procedure as of Granulation Example 3 was carried out except that the temperature of the ion-exchanged water, as used for the granulation, was changed from room temperature to 90° C. As a result, an adhesion of the water-absorbent resin to the mixer, which had slightly been seen in Granulation Example 3, was hardly seen in the present granulation example, so the continuous granulation ability was further improved.

Comparative Example 1-4

Surface-crosslinking of Water-absorbent Resin Granule Alone

A surface-crosslinking agent, comprising 0.05 parts by weight of ethylene glycol diglycidyl ether, 0.75 parts by weight of glycerol, 3 parts by weight of water, 0.75 parts by weight of isopropanol, and 0.5 parts by weight of lactic acid, was mixed with 100 parts by weight of the water-absorbent resin granule (3) as obtained in Granulation Example 3. The resultant mixture was heated at 200° C. for 40 minutes, thus obtaining a comparative water-absorbent resin composition (4) with a water absorption capacity of 28 g/g and an absorption capacity of 23 g/g under a load.

Comparative Example 1-5

Surface-crosslinking of Primary Particle Alone

A comparative water-absorbent resin composition (5) was obtained by carrying out the same surface-crosslinking as of Comparative Example 1-4 to 100 parts by weight of the water-absorbent resin powder ($B_1$) which was a primary particle as obtained in Production Example 1-2. The resultant comparative water-absorbent resin composition (5) showed a water absorption capacity of 28 g/g and an absorption capacity of 25 g/g under a load.

Comparative Example 1-6

Surface-crosslinking of Mixture of Primary Particle and Fine Powder

A comparative water-absorbent resin composition (6) was obtained by carrying out the same surface-crosslinking as of Comparative Example 1-4 to the water-absorbent resin powder (B) with a particle diameter smaller than 850 μm as obtained in Production Example 1-2 above. The resultant comparative water-absorbent resin composition (6) showed a water absorption capacity of 28 g/g and an absorption capacity of 22 g/g under a load.

Example 1-2

Surface-crosslinking of Particle Mixture

A water-absorbent resin composition (2) was obtained by carrying out the same procedure as of Comparative Example 1-2 to 100 parts by weight of a particle mixture comprising 13.7 parts by weight of the water-absorbent resin granule (3) as obtained in Granulation Example 3 and 86.3 parts by weight of the water-absorbent resin powder ($B_1$) which was a primary particle as obtained in Production Example 1-2. The resultant water-absorbent resin composition (2) showed a water absorption capacity of 28 g/g and an absorption capacity of 25 g/g under a load.

Example 1-3

Surface-Crosslinking of Particle Mixture

The water-absorbent resin powder (1), as obtained in Example 2-1 below, was classified with a sieve of the mesh size of 500 μm and a sieve of the mesh size of 150 μm, thus obtaining a water-absorbent resin granule with a particle diameter of 500 to 150 μm. Then, a water-absorbent resin composition (3) was obtained by carrying out the same procedure as of Comparative Example 1-1 to 100 parts by weight of a particle mixture comprising 15 parts by weight of the water-absorbent resin granule as obtained immediately above and 85 parts by weight of the water-absorbent resin powder ($A_1$) which was a primary particle as obtained in Production Example 1-1.

Example 1-4

Mixing of Surface-crosslinked Product of Water-absorbent Resin Primary Particle and Surface-Crosslinked Product of Water-Absorbent Resin Granule A water-absorbent resin composition (4) was obtained by uniformly mixing 40 parts by weight of the comparative water-absorbent resin composition (1), as obtained in Comparative Example 1-1, with 60 parts by weight of the comparative water-absorbent resin composition (5) as obtained in Comparative Example 1-5.

Results of the Examples and the Comparative Examples, as mentioned above, are shown in Table 1.

As is shown in Table 1, the water-absorbent resin compositions, according to the present invention, show an excellent absorption of at least 25 g/g even under a high load of 50 g/cm² unlike conventional ones not according to the present invention, and further are very excellent in the absorption speed and the particle size distribution because of the granule content. In addition, as to the examples in which the particle mixtures were used according to the present invention, because the primary particle with high mechanical strength supports the entire composition, the fracture of the swollen gel that is seen in Comparative Examples 1-1 and 1-4 (cases of granule alone) is substantially not seen.

TABLE 1

| | Water absorption capacity (g/g) | Absorption capacity under load (g/g) | Water absorption speed (seconds) | Gel fracture | Granulation fracture ratio (%) |
|---|---|---|---|---|---|
| Comparative Example 1-1 (granule alone) | 33 | 27 | 50 | seen | 2.5 |
| Comparative Example 1-2 (powder ($A^1$) alone) | 33 | 27 | 140 | none | 0 |
| Comparative Example 1-3 (powder (A)) | 33 | 24 | 120 | none | — |
| Example 1-1 (particle mixture) | 33 | 27 | 95 | none | 0.3 |
| Comparative Example 1-4 (granule alone) | 28 | 23 | 50 | seen | 2.1 |
| Comparative Example 1-5 (powder ($B_1$) alone) | 28 | 25 | 140 | none | 0 |
| Comparative Example 1-6 (powder (B)) | 28 | 22 | 120 | none | — |
| Example 1-2 (particle mixture) | 28 | 25 | 90 | none | 0.2 |
| Example 1-3 (particle mixture) | 33 | 27 | 85 | none | 0.1 |
| Example 1-4 (particle mixture) | 31 | 26 | 95 | partially seen | 0.9 |

In addition, the respective particle size distribution of the powder (B), the powder ($B_1$), the fine powder ($B_2$), and the granule (3), as obtained above, are shown in Table 2 below.

TABLE 2

| Particle size distribution (μm) | 850/500 | 500/300 | 300/150 | 150/75 | 75 or less |
|---|---|---|---|---|---|
| Powder (B) | 7.0 | 42.3 | 37.0 | 9.8 | 3.9 |
| Powder ($B_1$) | 8.1 | 49.1 | 42.9 | 0 | 0 |
| Fine powder ($B_2$) | 0 | 0 | 0 | 71.5 | 28.5 |
| Granule (3) | 19.7 | 58.0 | 15.6 | 5.2 | 2.4 |

Granulation Example 5

First, 400 g of the water-absorbent resin powder ($A_2$) with a particle diameter smaller than 150 μm, as obtained in Production Example 1-1, was placed into Lödige Mixer M-5 (trademark) of 5 liters as produced by Gebrüder Lödige Maschinenbau GmbH. Then, 600 g of water, as heated to 90° C., was injected from a funnel at once while rotating the impeller of the above mixer at a high speed using an alternating electric power source of 60 Hz/100 V.

The water-absorbent resin powder ($A_2$) was mixed with water within 10 seconds, and the resultant entire contents of the mixer was a gelatinous water-absorbent resin granule with a particle diameter of about 1 to about 5 mm. In the Lödige Mixer, the water-absorbent resin granule was in pieces, and there was no sign that the granule was kneaded by mixing with the impeller.

After the high-speed stirring in the Lödige Mixer for 1 minute, the resultant water-absorbent resin granule was separated from the mixer, and then dried in the same way as of Granulation Example 1. As a result, the granule was uniformly and sufficiently dried.

Next, the resultant dry granule was pulverized with the foregoing roller mill under the same conditions as those in Production Example 1-1, and then classified into particles with a particle diameter of 850 to 150 μm, thus obtaining a water-absorbent resin granule (5) with a water absorption capacity of 42 g/g and a water-soluble content of 10% by weight. The ratio of the water-absorbent resin granule with a particle diameter of 850 to 150 μm was 82% of the pulverization product.

A few particles of the water-absorbent resin granule (5) were extracted, and the physiological salt solution was then added dropwise to each particle, and the liquid-absorption behavior was then observed. As a result, the collapse to small fine particles was seen with the progress of swelling.

Granulation Example 6

A water-absorbent resin granule in pieces in the same state as of Granulation Example 1 was obtained in the same way as of Granulation Example 1 except that the amount of the heated water was 200 g. The resultant water-absorbent resin granule was treated in the same way as of Granulation Example 1 and then classified into particles with a particle diameter of 850 to 150 μm, thus obtaining a water-absorbent resin granule (6) with a water absorption capacity of 42 g/g and a water-soluble content of 11% by weight. The ratio of the water-absorbent resin granule (6) with a particle diameter of 850 to 150 μm was 80% of the pulverization product from the roller mill.

Granulation Example 7

A water-absorbent resin granule in pieces in the same state as of Granulation Example 1 was obtained in the same way as of Granulation Example 1 except that the amount of the heated water was 450 g. The resultant water-absorbent resin granule was treated in the same way as of Granulation Example 1 and then classified into particles with a particle diameter of 850 to 150 μm, thus obtaining a water-absorbent resin granule (7) with a water absorption capacity of 42 g/g and a water-soluble content of 10% by weight. The ratio of the water-absorbent resin granule (7) with a particle diameter of 850 to 150 μm was 84% of the pulverization product from the roller mill.

Granulation Example 8

A water-absorbent resin granule in pieces in the same state as of Granulation Example 1 was obtained in the same way as of Granulation Example 1 except that the temperature of the heated water was 70° C. The resultant water-absorbent resin granule was treated in the same way as of Granulation Example 1 and then classified into particles with a particle diameter of 850 to 150 μm, thus obtaining a water-absorbent resin granule (8) with a water absorption capacity of 42 g/g and a water-soluble content of 10% by weight. The ratio of the water-absorbent resin granule (8) with a particle diameter of 850 to 150 μm was 84% of the pulverization product from the roller mill.

Granulation Example 9

First, 300 g of water of 80° C. was placed into a mortar mixer of 5 liters (the temperature of a vessel of 5 liters in the mixer was kept with a bath of 80° C.) as produced by Nishi Nihon Shikenki Seisakusho K. K. Then, 200 g of the water-absorbent resin powder ($A_2$) with a particle diameter smaller than 150 μm, as obtained in Production Example 1-1, was added at once while rotating the impeller of the above mortar mixer at a high speed using an alternating electric power source of 60 Hz/100 V.

The water-absorbent resin powder ($A_2$) was mixed with water within 10 seconds, and the resultant entire contents of the mixer was a gelatinous water-absorbent resin granule with a particle diameter of about 3 to about 10 mm. In the mortar mixer, the water-absorbent resin granule was in pieces, and there was no sign that the granule was kneaded by mixing with the impeller.

After the high-speed stirring in the mortar mixer for 3 minutes, the resultant water-absorbent resin granule in pieces was separated from the mixer, and then placed on a wire net of the mesh size of 300 μm (50 mesh), and then dried in a hot-air circulation type dryer at 150° C. for 2 hours.

Next, the resultant dry granule was pulverized with the foregoing roller mill under the same conditions as those in Production Example 1-1, and then classified into particles with a particle diameter of 850 to 150 μm, thus obtaining a water-absorbent resin granule (9) with a water absorption capacity of 42 g/g and a water-soluble content of 10% by weight. The ratio of the water-absorbent resin granule (9) with a particle diameter of 850 to 150 μm was 84% of the pulverization product.

Granulation Example 10

Water was added to the water-absorbent resin powder ($A_2$) under high-speed stirring in the mortar mixer of 5 liters (produced by Nishi Nihon Shikenki Seisakusho K. K.) in the same way as of Granulation Example 1 except that the temperature of 300 g of water to be added to 200 g of the water-absorbent resin powder ($A_2$) was 20° C.

It took about 40 seconds to mix the water-absorbent resin powder ($A_2$) with water, and a huge united lumpy gel was formed, so no water-absorbent resin granule in pieces was obtained.

PRODUCTION EXAMPLE 2-1 FOR WATER-ABSORBENT RESIN POWDER

A reaction solution was prepared by dissolving polyethylene glycol diacrylate (average molecular weight: 478) of 0.05 mol % as an internal crosslinking agent into a 33 wt % aqueous solution of sodium acrylate (hydrophilic monomer) with a neutralization ratio of 75 mol %. Next, a nitrogen gas was introduced into this reaction solution to decrease the amount of dissolved oxygen therein to not more than 0.1 ppm. Then, the reaction solution was supplied into a reaction vessel as prepared by capping a stainless-steel-made double-arm type kneader having two sigma type wings and a jacket. The reaction solution was adjusted to 20° C., and the internal atmosphere of the reaction vessel was replaced with a nitrogen gas. Subsequently, while stirring the reaction solution, sodium persulfate and L-ascorbic acid were added thereto as polymerization initiators in ratios of 0.14 g/mol and 0.008 g/mol, respectively, relative to the sodium acrylate.

As a result, 1 minute after the addition of the polymerization initiators, a polymerization reaction got started and, 16 minutes after, the reaction solution reached the peak temperature of 83° C., when the resultant hydrogel polymer was a finely particulated one with a size of about 5 mm. Then, the stirring was further continued, and the reaction had been finished 60 minutes after the initiation of the polymerization, and the resultant finely particulated hydrogel polymer was then separated.

This finely-particulated hydrogel polymer was spread on a wire net and then dried at 160° C. with a hot-air dryer for 65 minutes. Then, the resultant dried product was pulverized with a roll granulator (made by Nippon Granulator K. K.), and then classified with a sieve of the mesh size of 500 μm, and further the residue of the dried product on the sieve was pulverized and classified again, thus obtaining an irregular pulverized water-absorbent resin powder (C) with an average particle diameter of 300 μm and a particle diameter distribution where the proportion of particles with a particle diameter of not larger than 105 μm was 15% by weight.

Then, the resultant water-absorbent resin powder (C) was classified with a sieve of the mesh size of 105 μm, thus obtaining a water-absorbent resin powder ($C_1$) with a particle diameter of 105 to 500 μm, but not including 105 μm, and a water-absorbent resin powder ($C_2$) with a particle diameter of not larger than 105 μm.

PRODUCTION EXAMPLE 2-2 FOR WATER-ABSORBENT RESIN POWDER

A reaction solution was prepared by dissolving polyethylene glycol diacrylate (average molecular weight: 478) of 0.04 mol % as an internal crosslinking agent into a 35 wt % aqueous solution of sodium acrylate (hydrophilic monomer) with a neutralization ratio of 65 mol %. Next, a nitrogen gas was introduced into this reaction solution to decrease the amount of dissolved oxygen therein to not more than 0.1 ppm.

Next, the reaction solution was injected in a thickness of 23 mm into a stainless butt of which the inner surface was coated with Teflon. Then, the upper portion of this stainless butt was sealed with an acrylic-resin-made cap having a nitrogen-introducing inlet, an exhaust ventage, and a polymerization-initiator-projecting inlet. Next, this stainless butt was immersed into a water bath of 18° C. to adjust the temperature of the reaction solution to 18° C. while introducing a nitrogen gas into the reaction solution to decrease the amount of dissolved oxygen therein to not more than 0.5 ppm. Subsequently, V-50 (azo type polymerization initiator made by Wako Pure Chemical Industries, Ltd.), L-ascorbic acid, and hydrogen peroxide were added as polymerization initiators to the reaction solution in ratios of 0.02 g/mol, 0.0018 g/mol, and 0.0014 g/mol, respectively, relative to the sodium acrylate, and they were mixed sufficiently.

As a result, 1 minute after the addition of the polymerization initiators, a polymerization reaction got started. After confirming the polymerization initiation, the above stainless butt was immersed into a water bath of 10° C. up to the height of 10 mm from the bottom of the stainless butt. Twelve minutes after the addition of the polymerization initiators, the reaction solution reached the peak temperature (82° C.). Then, the water bath of 10° C. was replaced with a water bath of 60° C., in which the stainless butt was held for 60 minutes to finish the reaction.

Then, the resultant hydrogel polymer was separated from the stainless butt and then pulverized with a meat chopper having dice of 9.5 mm in diameter (No. 32 model chopper made by Hiraga Kosakusho K. K.) and then dried at 160° C. for 65 minutes. Then, the resultant dried product was pulverized with a roll granulator (Nippon Granulator K. K.), and then classified with a sieve of the mesh size of 500 μm, and further the residue of the dried product on the sieve was pulverized and classified again, thus obtaining an irregular pulverized water-absorbent resin powder (D) with an average particle diameter of 280 μm and a particle diameter distribution where the proportion of particles with a particle diameter of not larger than 105 μm was 18% by weight.

Subsequently, an aqueous solution of surface-crosslinking agents, comprising 0.03 parts by weight of ethylene glycol diglycidyl ether, 1 part by weight of propylene glycol, 3 parts by weight of water, and 1 part by weight of isopropanol, was mixed with 100 parts by weight of the above water-absorbent resin powder (D). The resultant mixture was heated at 195° C. for 40 minutes, thus obtaining a surface-crosslinked water-absorbent resin powder (D').

Then, the resultant water-absorbent resin powder (D') was classified again with a sieve of the mesh size of 850 μm and a sieve of the mesh size of 105 μm, thus obtaining a water-absorbent resin powder ($D'_1$) with a particle diameter of 105 to 850 μm, but not including 105 μm, and a water-absorbent resin powder ($D'_2$) with a particle diameter of not larger than 105 μm.

Next, the water-absorbent resin powders with a particle diameter of not larger than 105 μm, as obtained in the above production examples, were granulated as follows:

Example 2-1

Air was supplied into the continuous extrusion mixer 1 of FIGS. 4 and 5 from one end portion thereof, namely, from the supplying-inlet 3 as made at the left end in FIG. 4, to keep the reduced pressure inside the casing 2 of the continuous extrusion mixer 1 not higher than 5 mmH$_2$O, while water as preheated to 80° C. was supplied at a rate of 165 kg/hr from the supplying-inlet 4 as made at a distance of 140 mm from the left end of the casing 2 wherein the entire length of the rotary shaft 11 present in the casing 2 of the continuous extrusion mixer 1 was 475 mm.

On the other hand, the water-absorbent resin powder ($C_2$), as obtained in Production Example 2-1, was supplied with a proportioning supply machine (made by Accu-Rate Inc.) at a rate of 110 kg/hr into the continuous extrusion mixer 1 from the supplying-inlet 8 as made at a distance of 228 mm from the left end of the rotary shaft 11 in the casing 2 (about 52% downstream of the discharge outlet 10 wherein the entire length of the rotary shaft 11 was 100%), and the stirring-members 12 were rotated at 1,000 rpm, thus continuously mixing the water-absorbent resin powder ($C_2$) and water.

As a result, a particulate hydrogel granule (1) with a particle diameter of 1 to 5 mm was continuously obtained from the discharge outlet 10 as made at the right end of the continuous extrusion mixer 1. At each time of (1) 10 minutes, (2) 30 minutes, and (3) 60 minutes after the mixing initiation, the mixing was stopped to measure the weight of the continuous extrusion mixer 1 to evaluate the amount of adhesive materials as adhered to inside the continuous extrusion mixer 1 along with such adhered state. As a result, at any time of (1) to (3) above, it was seen that only a small amount of a mixture of water and the water-absorbent resin powder ($C_2$) adhered mainly to the periphery of the supplying-inlet 8 in the continuous extrusion mixer 1, but that did not influence the mixing (stirring). In addition, at any time of (1) to (3) above, the weight of the above adhesive materials was in the range of 440 to 460 g.

Then, the resultant hydrogel granule (1) was spread on a wire net and then dried at 160° C. with a hot-air dryer for 65 minutes. Then, the resultant dried product was pulverized with a roller mill (made by Meiji Machine K. K.), and then classified with a sieve of the mesh size of 500 μm, and further the residue of the dried product on the sieve was pulverized and classified again in the same way as of Production Example 2-1, thus obtaining an irregular pulverized water-absorbent resin powder (1) with an average particle diameter of 300 μm and a particle diameter distribution where the proportion of particles with a particle diameter of not larger than 105 μm was 18% by weight, from which it would be understood that the above hydrogel granule (1) was a granule with almost as high a strength as a primary particle.

Example 2-2

The water-absorbent resin powder ($C_2$) and water were continuously mixed in the same way as of Example 2-1 except that the water-absorbent resin powder ($C_2$) was supplied into the continuous extrusion mixer 1 from the supplying-inlet 9 as made at a distance of 317 mm from the left end of the rotary shaft 11 in the casing 2 (about 33% downstream of the discharge outlet 10 wherein the entire length of the rotary shaft 11 was 100%).

As a result, a particulate hydrogel granule (2) with a particle diameter of 1 to 5 mm was continuously obtained from the discharge outlet 10 of the continuous extrusion mixer 1. Incidentally, the hydrogel granule (2) contained a small amount of fisheye-like water-absorbent resin powder (about 3% by weight) immediately after discharged from the discharge outlet 10, but became uniform soon.

In addition, an evaluation was made about the amount of adhesive materials as adhered to inside the continuous extrusion mixer 1 along with such adhered state in the same way as of Example 2-1. As a result, at any time, it was seen that only a small amount of a mixture of water and the water-absorbent resin powder ($C_2$) adhered mainly to the periphery of the supplying-inlet 9 in the continuous extrusion mixer 1, but that did not influence the mixing (stirring). In addition, at any time, the weight of the above adhesive materials was in the range of 450 to 470 g.

Then, the resultant hydrogel granule (2) was dried, pulverized, and classified in the same way as of Example 2-1, thus obtaining an irregular pulverized water-absorbent resin powder (2) with an average particle diameter of 300 μm and a particle diameter distribution where the proportion of particles with a particle diameter of not larger than 105 μm was 19% by weight, from which it would be understood that the above hydrogel granule (2) was a granule with almost as high a strength as a primary particle.

Example 2-3

The water-absorbent resin powder ($D'_2$) and water were continuously mixed in the same way as of Example 2-1 except that the water-absorbent resin powder ($C_2$) was replaced with the water-absorbent resin powder ($D'_2$) as obtained in Production Example 2-2.

As a result, a particulate hydrogel granule (3) with a particle diameter of 1 to 5 mm was continuously obtained from the discharge outlet 10 of the continuous extrusion mixer 1. An evaluation was made about the amount of adhesive materials as adhered to inside the continuous extrusion mixer 1 along with such adhered state in the same way as of Example 2-1. As a result, at any time, it was seen that only a small amount of a mixture of water and the water-absorbent resin powder ($D'_2$) adhered mainly to the periphery of the supplying-inlet 8 in the continuous extrusion mixer 1, but that did not influence the mixing (stirring). In addition, at any time, the weight of the above adhesive materials was in the range of 400 to 430 g.

Then, the resultant hydrogel granule (3) was dried, pulverized, and classified in the same way as of Production Example 2-2, thus obtaining an irregular pulverized water-absorbent resin powder (3) with an average particle diameter of 280 μm and a particle diameter distribution where the proportion of particles with a particle diameter of not larger than 105 μm was 20% by weight, from which it would be understood that the above hydrogel granule (3) was a granule with almost as high a strength as a primary particle.

Example 2-4

The water-absorbent resin powder ($C_2$) and water were continuously mixed in the same way as of Example 2-1 except that the supplying-rate of water was changed from 165 kg/hr to 260 kg/hr.

As a result, a particulate hydrogel granule (4) with a particle diameter of 1 to 5 mm was continuously obtained from the discharge outlet 10 of the continuous extrusion mixer 1. An evaluation was made about the amount of adhesive materials as adhered to inside the continuous extrusion mixer 1 along with such adhered state in the same way as of Example 2-1. As a result, at any time, it was seen that only a small amount of a mixture of water and the water-absorbent resin powder ($C_2$) adhered mainly to the periphery of the supplying-inlet 8 in the continuous extrusion mixer 1, but that did not influence the mixing (stirring). In addition, at any time, the weight of the above adhesive materials was in the range of 250 to 320 g.

Then, the resultant hydrogel granule (4) was dried, pulverized, and classified in the same way as of Example 2-1, thus obtaining an irregular pulverized water-absorbent resin powder (4) with an average particle diameter of 300 μm and a particle diameter distribution where the proportion of particles with a particle diameter of not larger than 105 μm was 15% by weight, from which it would be understood that the above hydrogel granule (4) was a granule with almost as high a strength as a primary particle.

Comparative Example 2-1

The water-absorbent resin powder ($C_2$) and water were continuously mixed in the same way as of Example 2-1 except that the water-absorbent resin powder ($C_2$) was supplied into the continuous extrusion mixer 1 from the supplying-inlet 3 as made at the left end in the casing 2, in other words, the water-absorbent resin powder ($C_2$) was supplied upstream of water.

As a result, a particulate comparative hydrogel granule (1) with a particle diameter of 1 to 10 mm was obtained from the discharge outlet 10 of the continuous extrusion mixer 1. The comparative hydrogel granule (1) contained a fisheye-like water-absorbent resin powder of about 15% by weight. An evaluation was made about the amount of adhesive materials as adhered to inside the continuous extrusion mixer 1 along with such adhered state in the same way as of Example 2-1. As a result, in 10 minutes after the mixing initiation, a large amount of a mixture of water and the water-absorbent resin powder ($C_2$) adhered mainly to the above supplying-inlet 3 and the stirring-members 12 . . . as located between the supplying-inlets 3 and 4, so the mixing became difficult to continue, when the weight of the above adhesive materials was 1,520 g.

Then, the resultant comparative hydrogel granule (1) was dried, pulverized, and classified in the same way as of Example 2-1, thus obtaining an irregular pulverized comparative water-absorbent resin powder (1) with a particle diameter distribution where the proportion of particles with a particle diameter of not larger than 105 μm was 25% by weight.

Comparative Example 2-2

The water-absorbent resin powder ($C_2$) and water were continuously mixed in the same way as of Example 2-1 except that the water-absorbent resin powder ($C_2$) was supplied into the continuous extrusion mixer 1 from the supplying-inlet 7 as was made at a distance of 140 mm from the left end of the rotary shaft 11 in the casing 2 and was different from the supplying-inlet 4, in other words, the water-absorbent resin powder ($C_2$) and water were supplied from the same position, but separately.

As a result, a particulate comparative hydrogel granule (2) with a particle diameter of 1 to 10 mm was obtained from the discharge outlet 10 of the continuous extrusion mixer 1. The comparative hydrogel granule (2) contained a fisheye-like water-absorbent resin powder of about 10% by weight. An evaluation was made about the amount of adhesive materials as adhered to inside the continuous extrusion mixer 1 along with such adhered state in the same way as of Example 2-1. As a result, a mixture of water and the water-absorbent resin powder ($C_2$) adhered mainly to the periphery of the supplying-inlet 7 and to upstream thereof, namely, to the stirring-members 12 . . . as located between the supplying-inlets 3 and 7, in the continuous extrusion mixer 1, and therefore, 30 minutes after the mixing initiation, the mixing became difficult to continue, when the weight of the above adhesive materials was 1,300 g.

Then, the resultant comparative hydrogel granule (2) was dried, pulverized, and classified in the same way as of Example 2-1, thus obtaining an irregular pulverized comparative water-absorbent resin powder (2) with a particle diameter distribution where the proportion of particles with a particle diameter of not larger than 105 μm was 22% by weight.

Example 2-5

The water-absorbent resin powder ($C_2$) and water were continuously mixed in the same way as of Example 2-1 except that the supplying-rate of the water-absorbent resin powder ($C_2$) was changed from 110 kg/hr to 65 kg/hr, and that the supplying-rate of water was changed from 165 kg/hr to 65 kg/hr, and that the temperature of water was changed from 80° C. to 70° C.

As a result, a particulate hydrogel granule (5) with a particle diameter of 1 to 5 mm was continuously obtained from the discharge outlet 10 of the continuous extrusion mixer 1. An evaluation was made about the amount of adhesive materials as adhered to inside the continuous extrusion mixer 1 along with such adhered state in the same way as of Example 2-1. As a result, at any time, it was seen that only a small amount of a mixture of water and the water-absorbent resin powder ($C_2$) adhered mainly to the periphery of the supplying-inlet 8 in the continuous extrusion mixer 1, but that did not influence the mixing (stirring). In addition, at any time, the weight of the above adhesive materials was in the range of 500 to 550 g.

Then, the resultant hydrogel granule (5) was dried, pulverized, and classified in the same way as of Example 2-1, thus obtaining an irregular pulverized water-absorbent resin powder (5) with an average particle diameter of 310 μm and a particle diameter distribution where the proportion of particles with a particle diameter of not larger than 105 μm was 20% by weight, from which it would be understood that the above hydrogel granule (5) was a granule with almost as high a strength as a primary particle.

Example 2-6

The water-absorbent resin powder ($D'_2$) and water were continuously mixed in the same way as of Example 2-3 except that the supplying-rate of the water-absorbent resin powder ($D'_2$) was changed from 110 kg/hr to 66 kg/hr, and that the supplying-rate of water was changed from 165 kg/hr to 54 kg/hr, and that the temperature of water was changed from 80° C. to 90° C., and that the revolution number of the stirring-members 12 was changed from 1,000 rpm to 1,500 rpm.

As a result, a particulate hydrogel granule (6) with a particle diameter of 1 to 5 mm was continuously obtained from the discharge outlet 10 of the continuous extrusion mixer 1. An evaluation was made about the amount of adhesive materials as adhered to inside the continuous extrusion mixer 1 along with such adhered state in the same way as of Example 2-1. As a result, at any time, it was seen that only a small amount of a mixture of water and the water-absorbent resin powder ($D'_2$) adhered mainly to the periphery of the supplying-inlet 8 in the continuous extrusion mixer 1, but that did not influence the mixing (stirring). In addition, at any time, the weight of the above adhesive materials was in the range of 600 to 650 g.

Then, the resultant hydrogel granule (6) was dried, pulverized, and classified in the same way as of Production Example 2-2, thus obtaining an irregular pulverized water-absorbent resin powder (6) with an average particle diameter of 290 μm and a particle diameter distribution where the proportion of particles with a particle diameter of not larger than 105 μm was 21% by weight, from which it would be understood that the above hydrogel granule (6) was a granule with almost as high a strength as a primary particle.

From the results of Examples 2-1 to 2-6 and Comparative Examples 2-1 to 2-2, it would be understood that if the water-absorbent resin powder is supplied downstream of water, then a stable mixing can be carried out, for a long term, and further the amount of the formation of the fine powder, as included in the water-absorbent resin powder as obtained by drying and pulverizing the resultant hydrogel granule, can be reduced (in other words, the granulation strength can be enhanced still more), when compared with the case where the water-absorbent resin powder is supplied upstream of water or where the supplying-position of the water-absorbent resin powder and that of water are made even.

In addition, as to Comparative Examples 2-1 and 2-2, the residence time of the water-absorbent resin powder ($C_2$) in the continuous extrusion mixer 1 was longer than that in Example 2-1, whereas fisheyes were included in the resultant hydrogel granule. From this result, it can be guessed that when the water-absorbent resin powder is supplied upstream of water or at the same position as water, partial unevenness occurs in the contact between the water-absorbent resin powder and water, and that this is a factor in failure to make a stable mixing for a long term.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A water-absorbent resin composition, which comprises a product obtained by surface-crosslinking a mixture of a water-absorbent resin primary particle and a water-absorbent resin granule.

2. A water-absorbent resin composition according to claim 1, wherein the water-absorbent resin granule is a granule as obtained by mixing 100 parts by weight of a water-absorbent resin powder with 80 to 280 parts by weight of an aqueous liquid.

3. A water-absorbent resin composition according to claim 1, wherein the ratio by weight of the water-absorbent resin primary particle to the water-absorbent resin granule is in the range of 95/5 to 40/60.

4. A water-absorbent resin composition, which comprises a mixture of a surface-crosslinked product of a water-absorbent resin primary particle and a surface-crosslinked product of a water-absorbent resin granule.

5. A water-absorbent resin composition according to claim 4, wherein the water-absorbent resin granule is a granule as obtained by mixing 100 parts by weight of a water-absorbent resin powder with 80 to 280 parts by weight of an aqueous liquid.

6. A water-absorbent resin composition according to claim 4, wherein the ratio by weight of the water-absorbent resin primary particle to the water-absorbent resin granule is in the range of 95/5 to 40/60.

7. A water-absorbent resin composition, which comprises a mixture of a water-absorbent resin primary particle and a water-absorbent resin granule and has an absorption capacity of at least 25 g/g for a physiological salt solution under a load of 50 g/cm$^2$.

8. A water-absorbent resin composition according to claim 7, wherein the water-absorbent resin granule is a granule as obtained by mixing 100 parts by weight of a water-absorbent resin powder with 80 to 280 parts by weight off an aqueous liquid.

9. A water-absorbent resin composition according to claim 7, wherein the ratio by weight of the water-absorbent resin primary particle to the water-absorbent resin granule is in the range of 95/5 to 40/60.

10. A process for producing a water-absorbent resin composition, comprising the step of adding a crosslinking agent to a mixture of a water-absorbent resin primary particle and a water-absorbent resin granule, thus crosslinking the surface neighborhood of the mixture.

11. A process according to claim 10 wherein an average particle diameter of the water-absorbent resin primary particle and/or an average particle diameter of the water-absorbent resin granule is in a range of 200 to 600 μm, which is determined by a classification using JIS standard sieves.

12. A process for producing a water-absorbent resin composition, comprising the step of mixing a surface-crosslinked product of a water-absorbent resin primary particle and a surface-crosslinked product of a water-absorbent resin granule.

13. A process according to claim 12, wherein an average particle diameter of the water-absorbent resin primary particle and/or an average particle diameter of the water-absorbent resin granule is in a range of 200 to 600 μm, which is determined by a classification using JIS standard sieves.

14. A water-absorbent resin composition according to claim 7, wherein a proportion of particles having a particle size of 850 to 150 μm is 95% by weight or higher, which is determined by a classification using JIS standard sieves.

15. A water-absorbent resin composition according to claim 7, wherein the water-absorbent resin composition has an absorption speed of 100 seconds or less, which is defined as a number of seconds of a time for 0.358 g of the water-absorbent resin composition to absorb all of an artificial urine of 10.00 g.

16. A water-absorbent resin composition according to claim 14, wherein the water-absorbent resin composition has a granulation fracture ratio of 10% or less, which is defined as a ratio of particles having a particle diameter of less than 150 μm, which is determined by a classification using JIS standard sieves, after a fracture by applying an impact force.

17. A water-absorbent resin composition according to claim 7, wherein the water-absorbent resin composition has a water-soluble content of 15% by weight or lower.

18. A water-absorbent resin composition according to claim 1, wherein a proportion of particles having a particle size of 850 to 150 μm is 95% by weight or higher, which is determined by a classification using JIS standard sieves.

19. A water-absorbent resin composition according to claim 4, wherein a proportion of particles having a particle size of 850 to 150 μm is 95% by weight or higher, which is determined by a classification using JIS standard sieves.

20. A process according to claim 10, wherein, in the water-absorbent resin composition, a proportion of particles having a particle size of 850 to 150 μm is 95% by weight or higher, which is determined by a classification using JIS standard sieves.

21. A process according to claim 12, wherein, in the water-absorbent resin composition, a proportion of particles having a particle size of 850 to 150 μm is 95% by weight or higher, which is determined by a classification using JIS standard sieves.

* * * * *